US011331080B2

(12) United States Patent
Noguchi

(10) Patent No.: US 11,331,080 B2
(45) Date of Patent: May 17, 2022

(54) ULTRASOUND DIAGNOSTIC APPARATUS THAT GENERATES AN ULTRASOUND IMAGE USING A HARMONIC IMAGING METHOD AND METHOD OF CONTROLLING ULTRASOUND DIAGNOSTIC APPARATUS THAT GENERATES AN ULTRASOUND IMAGE USING A HARMONIC IMAGING

(71) Applicant: FUJIFILM Corporation, Tokyo (JP)

(72) Inventor: Masafumi Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/011,123

(22) Filed: Sep. 3, 2020

(65) Prior Publication Data

US 2020/0397411 A1 Dec. 24, 2020

Related U.S. Application Data

(63) Continuation of application No. PCT/JP2019/009615, filed on Mar. 11, 2019.

(30) Foreign Application Priority Data

Mar. 20, 2018 (JP) .............................. JP2018-052200

(51) Int. Cl.
*A61B 8/08* (2006.01)
*A61B 8/14* (2006.01)
(Continued)

(52) U.S. Cl.
CPC .............. *A61B 8/5276* (2013.01); *A61B 8/14* (2013.01); *A61B 8/4488* (2013.01); *A61B 8/54* (2013.01);
(Continued)

(58) Field of Classification Search
CPC ....... A61B 8/5276; A61B 8/4488; A61B 8/54; A61B 8/14; G01S 7/5202–52022; G01S 7/52046; G01S 7/8915
See application file for complete search history.

(56) References Cited

U.S. PATENT DOCUMENTS 6,193,662 B1 * 2/2001 Hwang ............... G01S 7/52026
600/447
6,319,203 B1 * 11/2001 Averkiou ............ G01S 7/52038
600/443
(Continued)

FOREIGN PATENT DOCUMENTS

EP      2287632 A1 *  2/2011  ......... G01S 15/8952
JP    2001-286472 A    10/2001
(Continued)

OTHER PUBLICATIONS

L. F. Nock et al., "Synthetic Receive Aperture Imaging with Phase Correction for Motion and for Tissue Inhomogeneities—Part I: Basic Principles," IEEE Transactions on Ultrasonics, Ferroelectrics, and Frequency Control, vol. 39, No. 4, pp. 489-495, Jul. 1992 (Year: 1992).*

(Continued)

*Primary Examiner* — Oommen Jacob
*Assistant Examiner* — Nyrobi Celestine
(74) *Attorney, Agent, or Firm* — Studebaker & Brackett PC

(57) ABSTRACT

An ultrasound diagnostic apparatus 1 includes a transducer array 2, a transmission unit 3 that transmits an ultrasonic pulse FP and an ultrasonic pulse SP having phases inverted from each other on the scanning line from the transducer array 2 multiple times, a reception unit 4 that acquires reception signals from an output signal of the transducer array 2, a quadrature detection unit 5 that performs quadrature detection on the reception signals to acquire IQ signal
(Continued)

strings, a tissue velocity detection unit 6 that detects a velocity of a tissue in a subject based on the IQ signal strings, a phase correction unit 7 that corrects phases of the IQ signal strings, a pulse inversion addition unit 8 that adds IQ signals corresponding to the ultrasonic pulse FP and IQ signals corresponding to the ultrasonic pulse SP using the corrected IQ signal strings to acquire added signals, and an image generation unit 10 that generates an ultrasound image from the added signals.

12 Claims, 14 Drawing Sheets

(51) Int. Cl.
  *A61B 8/00* (2006.01)
  *G01S 7/52* (2006.01)
  *G01S 15/89* (2006.01)
(52) U.S. Cl.
  CPC ........ *G01S 7/5202* (2013.01); *G01S 7/52046* (2013.01); *G01S 15/8915* (2013.01)

(56) References Cited

U.S. PATENT DOCUMENTS

| | | | |
|---|---|---|---|
| 9,173,640 B2 * | 11/2015 | Lin | A61B 8/06 |
| 2001/0034485 A1 | 10/2001 | Kawagishi et al. | |
| 2002/0147398 A1 | 10/2002 | Kawagishi et al. | |
| 2003/0018259 A1 | 1/2003 | Kawagishi et al. | |
| 2003/0176792 A1 | 9/2003 | Kawagishi et al. | |
| 2003/0229285 A1 | 12/2003 | Simpson et al. | |
| 2005/0055178 A1 * | 3/2005 | Phillips | G01S 7/52039 702/189 |
| 2009/0245785 A1 * | 10/2009 | Asano | H04B 10/677 398/25 |
| 2011/0295116 A1 | 12/2011 | Lee | |
| 2013/0245445 A1 | 9/2013 | Kakee et al. | |
| 2019/0282212 A1 * | 9/2019 | Rosenzweig | A61B 8/5276 |

FOREIGN PATENT DOCUMENTS

| | | |
|---|---|---|
| JP | 2001-299765 A | 10/2001 |
| JP | 2002-143158 A | 5/2002 |
| JP | 2002-301068 A | 10/2002 |
| JP | 2003-230559 A | 8/2003 |

OTHER PUBLICATIONS

W. Wilkening et al., "Phase-Coded Pulse Sequence for Non-Linear Imaging," IEEE Ultrasonics Symposium, pp. 1559-1562, 2000 (Year: 2000).*

Shen, Che-Chou et al., "Pulse Inversion Techniques in Ultrasonic Nonlinear Imaging"; Journal of Medical Ultrasound, Elsevier; vol. 13, No. 1; Jan. 1, 2005; pp. 3-17; Amsterdam, the Netherlands.

Extended European Search Report issued in EP19772589.8 by the European Patent Office dated Apr. 19, 2021, which is related to U.S. Appl. No. 17/011,123.

May 1989, vol. 30 no. 3, pp. 225-231, non official translation (YOSHIKAWA, Yoshihiro, "Information processing in ultrasonic wave medical diagnosis", Journal of Information Processing Society of Japan).

Jul. 1987, D vol. J70D No. 7, pp. 1432-1440, non-official translation (NAMEKAWA, Koroku, "Real-time blood flow imaging equipment by ultrasonic Doppler", Proceedings of IEICE).

International Search Report issued in PCT/JP2019/009615; dated May 21, 2019.

Written Opinion issued in PCT/JP2019/009615; dated May 21, 2019.

An Office Action; "Notice of Reasons for Refusal", mailed by the Japanese Patent Office dated Sep. 14, 2021, which corresponds to Japanese Patent Application No. 2020-508219 and is related to U.S. Appl. No. 17/011,123; with English language translation.

An Office Action; "Notice of Reasons for Refusal", mailed by the Japanese Patent Office dated Mar. 8, 2022, which corresponds to Japanese Patent Application No. 2020-508219 and is related to U.S. Appl. No. 17/011,123; with English language translation.

* cited by examiner

ULTRASOUND DIAGNOSTIC APPARATUS THAT GENERATES AN ULTRASOUND IMAGE USING A HARMONIC IMAGING METHOD AND METHOD OF CONTROLLING ULTRASOUND DIAGNOSTIC APPARATUS THAT GENERATES AN ULTRASOUND IMAGE USING A HARMONIC IMAGING

CROSS-REFERENCE TO RELATED APPLICATIONS

This application is a Continuation of PCT International Application No. PCT/JP2019/009615 filed on Mar. 11, 2019, which claims priority under 35 U.S.C. § 119(a) to Japanese Patent Application No. 2018-052200 filed on Mar. 20, 2018. The above application is hereby expressly incorporated by reference, in its entirety, into the present application.

BACKGROUND OF THE INVENTION

1. Field of the Invention

The present invention relates to an ultrasound diagnostic apparatus and a method of controlling an ultrasound diagnostic apparatus, and in particular, to an ultrasound diagnostic apparatus and a method of controlling an ultrasound diagnostic apparatus that generate an ultrasound image using a harmonic imaging method.

2. Description of the Related Art

In a medical ultrasound diagnostic apparatus, in a case where a contrast medium is introduced into a subject to perform diagnosis, or the like, as disclosed in JP2002-301068A and JP2003-230559A, there is known a so-called harmonic imaging method that uses nonlinearity of the contrast medium, and extracts and images a nonlinear component from an ultrasound echo received by a transducer array. With the use of the harmonic imaging method, an image having high contrast in a tissue of the subject and the contrast medium can be generated.

In the harmonic imaging method, as a method of extracting the nonlinear component from the ultrasound echo, for example, there is known a pulse inversion method that sequentially transmits a first ultrasonic pulse and a second ultrasonic pulse having phases inverted from each other on the same scanning line, and adds a reception signal of the first ultrasonic pulse and a reception signal of the second ultrasonic pulse.

SUMMARY OF THE INVENTION

With the pulse inversion method, a fundamental component can be eliminated from the ultrasound echo to extract the nonlinear component.

However, in a case where a tissue of the subject having motion due to pulsation, respiration, or the like is imaged, the fundamental component of the ultrasound echo is also affected by the motion of the tissue. Accordingly, it is not possible to sufficiently eliminate the fundamental component from the ultrasound echo only by adding the reception signals of the first ultrasonic pulse and the second ultrasonic pulse having phases inverted from each other using the pulse inversion method, and there is a problem in that a so-called motion artifact is generated on an image.

The invention has been accomplished in order to solve such a problem in the related art, and an object of the invention is to provide an ultrasound diagnostic apparatus and a method of controlling an ultrasound diagnostic apparatus capable of reducing the occurrence of a motion artifact.

In order to achieve the above-described object, the invention provides an ultrasound diagnostic apparatus comprising a transducer array, a transmission unit that transmits a set of a first ultrasonic pulse and a second ultrasonic pulse having phases inverted from each other on the same scanning line from the transducer array into a subject N times equal to or greater than at least two times, a reception unit that acquires reception signals based on a signal output from the transducer array received an ultrasound echo generated in the subject, a quadrature detection unit that acquires an IQ signal string corresponding to the first ultrasonic pulse and an IQ signal string corresponding to the second ultrasonic pulse by performing quadrature detection in a determined range on the reception signals acquired by the reception unit, a tissue velocity detection unit that detects a velocity of a tissue in the subject based on the IQ signal strings acquired by the quadrature detection unit, a phase correction unit that corrects phases of the IQ signal strings obtained from each reflection position in the subject based on the velocity of the tissue detected by the tissue velocity detection unit such that an influence of the velocity of the tissue is cancelled, a pulse inversion addition unit that acquires added signals with a fundamental component eliminated by adding IQ signals corresponding to the first ultrasonic pulse and IQ signals corresponding to the second ultrasonic pulse adjacent in time series using the IQ signal strings with the phases corrected by the phase correction unit, and an image generation unit that generates an ultrasound image based on the added signal acquired by the pulse inversion addition unit.

The tissue velocity detection unit may detect the velocity of the tissue in the subject using a velocity vector at each reflection position calculated by autocorrelation from the IQ signal string having a positive phase between the IQ signal strings acquired by the quadrature detection unit and a velocity vector at each reflection position calculated by autocorrelation from the IQ signal string having a negative phase between the IQ signal strings acquired by the quadrature detection unit.

Alternatively, the tissue velocity detection unit may detect the velocity of the tissue in the subject using a velocity vector at each reflection position calculated by autocorrelation from IQ signal strings obtained by performing subtraction of the IQ signals corresponding to the first ultrasonic pulse and the IQ signals corresponding to the second ultrasonic pulse adjacent in time series.

The pulse inversion addition unit may acquire the added signals by performing both of addition of the IQ signals corresponding to each first ultrasonic pulse and the IQ signals corresponding to the second ultrasonic pulse immediately after IQ signals corresponding to the first ultrasonic pulse in time series and addition of the IQ signals corresponding to each second ultrasonic pulse and the IQ signals corresponding to the first ultrasonic pulse immediately after the IQ signals corresponding to the second ultrasonic pulse in time series.

Alternatively, the pulse inversion addition unit may acquire the added signals by only one of addition of the IQ signals corresponding to each first ultrasonic pulse and the IQ signals corresponding to the second ultrasonic pulse immediately after the IQ signals corresponding to the first ultrasonic pulse in time series or addition of the IQ signals corresponding to each second ultrasonic pulse and the IQ signals corresponding to the first ultrasonic pulse immediately after the second ultrasonic pulse in time series.

The ultrasound diagnostic apparatus may further comprise a tissue signal filter unit that eliminates a signal due to the tissue in the subject from the added signals acquired by the pulse inversion addition unit.

The ultrasound diagnostic apparatus may further comprise a nonlinear signal information calculation unit that calculates at least one of power or a velocity of a nonlinear signal from the added signals acquired by the pulse inversion addition unit.

In this case, it is preferable that the image generation unit generates the ultrasound image based on at least one of the power or the velocity of the nonlinear signal calculated by the nonlinear signal information calculation unit.

The transmission unit may transmit the set of the first ultrasonic pulse and the second ultrasonic pulse on each scanning line N times, and then, transmits the set of the first ultrasonic pulse and the second ultrasonic pulse on the next scanning line N times.

Alternatively, the transmission unit may transmit the set of the first ultrasonic pulse and the second ultrasonic pulse on a determined number of scanning lines N times by repeating one-time sequential transmission of the first ultrasonic pulse on the determined number of scanning lines and then one-time sequential transmission of the second ultrasonic pulse on the determined number of scanning lines N times.

Alternatively, the transmission unit may transmit the set of the first ultrasonic pulse and the second ultrasonic pulse on a determined number of scanning lines N times by repeating one-time sequential transmission of the set of the first ultrasonic pulse and the second ultrasonic pulse on the determined number of scanning lines N times.

It is preferable that the ultrasound diagnostic apparatus may further comprise a display unit that displays the ultrasound image.

The invention provides a method of controlling an ultrasound diagnostic apparatus comprising transmitting a set of a first ultrasonic pulse and a second ultrasonic pulse having phases inverted from each other on the same scanning line from a transducer array into a subject N times equal to or greater than at least two times, acquiring reception signals based on a signal output from the transducer array received an ultrasound echo generated in the subject, acquiring an IQ signal string corresponding to the first ultrasonic pulse and an IQ signal string corresponding to the second ultrasonic pulse by performing quadrature detection in a determined range on the acquired reception signals, detecting a velocity of a tissue in the subject based on the acquired IQ signal strings, correcting phases of the IQ signal strings obtained from each reflection position in the subject based on the detected velocity of the tissue such that an influence of the velocity of the tissue is cancelled, acquiring added signals with a fundamental component eliminated by adding IQ signals corresponding to the first ultrasonic pulse and IQ signals corresponding to the second ultrasonic pulse adjacent in time series using the IQ signal strings with the phases corrected, and generating an ultrasound image based on the acquired added signals.

According to the invention, since the ultrasound diagnostic apparatus includes the tissue velocity detection unit that detects the velocity of the tissue in the subject based on the IQ signal strings acquired by the quadrature detection unit, the phase correction unit that corrects phases of the IQ signal strings from each reflection position in the subject based on the velocity of the tissue detected by the tissue velocity detection unit such that an influence of the velocity of the tissue is cancelled, and the pulse inversion addition unit that acquires the added signals with a fundamental component eliminated by adding the IQ signals corresponding to the first ultrasonic pulse and the IQ signals corresponding to the second ultrasonic pulse adjacent in time series using the IQ signal strings having the phases corrected by the phase correction unit, the occurrence of a motion artifact can be reduced.

DESCRIPTION OF THE PREFERRED EMBODIMENTS

Hereinafter, embodiments of the invention will be described referring to the accompanying drawings. In the following description, it is assumed that a contrast medium is introduced into a subject.

Embodiment 1

Figure 1:
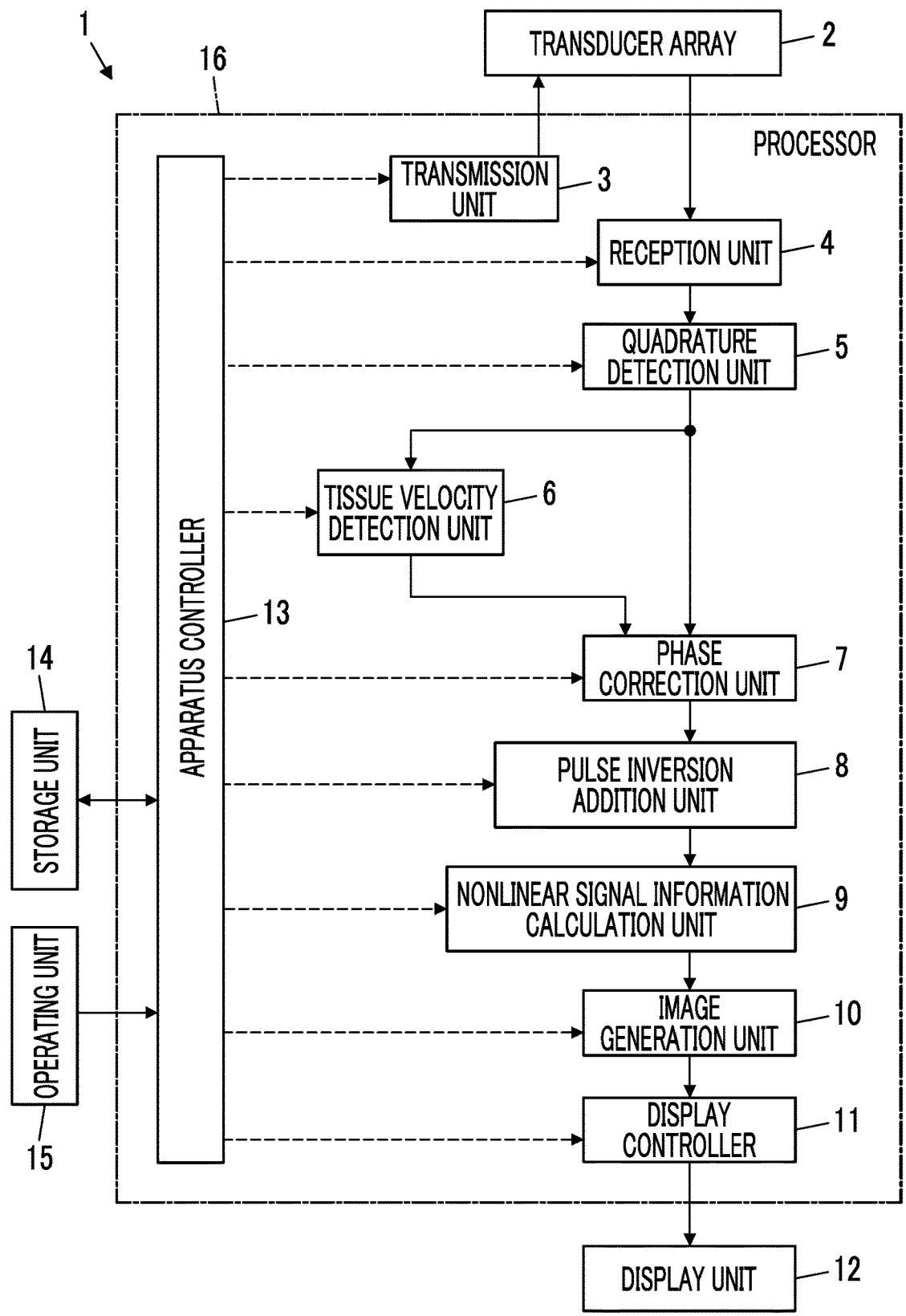
FIG. 1 is a block diagram showing the configuration of an ultrasound diagnostic apparatus according to Embodiment 1 of the invention.

FIG. 1 shows the configuration of an ultrasound diagnostic apparatus 1 according to Embodiment 1 of the invention. As shown in FIG. 1, the ultrasound diagnostic apparatus 1 comprises a transducer array 2, and a transmission unit 3 and a reception unit 4 are connected to the transducer array 2. A quadrature detection unit 5 is connected to the reception unit 4, and a tissue velocity detection unit 6 and a phase correction unit 7 are connected to the quadrature detection unit 5. The tissue velocity detection unit 6 is connected to the phase correction unit 7. A pulse inversion addition unit 8, a nonlinear signal information calculation unit 9, an image generation unit 10, a display controller 11, and a display unit 12 are sequentially connected to the phase correction unit 7.

An apparatus controller 13 is connected to the transmission unit 3, the reception unit 4, the quadrature detection unit 5, the tissue velocity detection unit 6, the phase correction unit 7, the pulse inversion addition unit 8, the nonlinear signal information calculation unit 9, the image generation unit 10, and the display controller 11, and a storage unit 14 and an operating unit 15 are connected to the apparatus controller 13. The apparatus controller 13 and the storage unit 14 are connected to perform bidirectional transfer of information to each other.

The transmission unit 3, the reception unit 4, the quadrature detection unit 5, the tissue velocity detection unit 6, the phase correction unit 7, the pulse inversion addition unit 8, the nonlinear signal information calculation unit 9, the image generation unit 10, the display controller 11, and the apparatus controller 13 constitute a processor 16.

The transducer array 2 of the ultrasound diagnostic apparatus 1 shown in FIG. 1 has a plurality of transducers arranged in a one-dimensional or two-dimensional manner. Each transducer transmits an ultrasonic wave in response to an actuation signal supplied from the transmission unit 3, receives an ultrasound echo from a subject, and outputs a signal based on the ultrasound echo. Each transducer is constituted by forming electrodes at both ends of a piezoelectric body made of, for example, piezoelectric ceramic represented by lead zirconatetitanate (PZT), a polymer piezoelectric element represented by poly vinylidene di fluoride (PVDF), piezoelectric single crystal represented by lead magnesium niobate-lead titanate (PMN-PT), or the like.

The transmission unit 3 of the processor 16 includes, for example, a plurality of pulse generators, and adjusts a delay amount of each drive voltage based on a transmission delay pattern selected according to a control signal from the apparatus controller 13 such that the ultrasonic waves transmitted from a plurality of transducers of the transducer array 2 form ultrasonic beam, and supplies the drive voltages to a plurality of transducers. In this way, in a case where the pulsed drive voltage is applied to the electrodes of each of a plurality of transducers of the transducer array 2, the piezoelectric body expands and contracts to generate a pulsed ultrasonic wave from the transducer, and a pulsed ultrasonic beam, that is, an ultrasonic pulse is formed from a combined wave of the ultrasonic waves. The transmission unit 3 sequentially generates a first ultrasonic pulse and a second ultrasonic pulse having phases inverted from each other from the transducer array 2 in this manner, and transmits a set of the first ultrasonic pulse and the second ultrasonic pulse into the subject along the same scanning line through the transducer array 2 multiple times.

The first ultrasonic pulse and the second ultrasonic pulse transmitted into the subject are reflected, for example, from a target, such as a part of the subject, and propagate through the subject toward the transducer array 2 as a so-called ultrasound echo. The ultrasound echo propagating toward the transducer array 2 is received by each transducer constituting the transducer array 2. In this case, each transducer constituting the transducer array 2 expands and contracts with reception of the propagating ultrasound echo to generate an electrical signal, and output the electrical signal to the reception unit 4.

Figure 2:
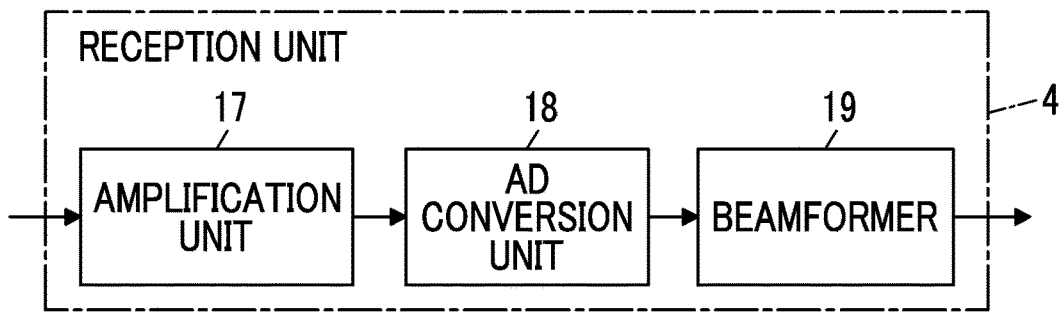
FIG. 2 is a block diagram showing the internal configuration of a reception unit in Embodiment 1 of the invention.

The reception unit 4 of the processor 16 executes processing of the signals output from the transducer array 2 in response to a control signal from the apparatus controller 13. As shown in FIG. 2, the reception unit 4 has a configuration in which an amplification unit 17, an analog-digital (AD) conversion unit 18, and a beamformer 19 are connected in series.

The amplification unit 17 of the reception unit 4 amplifies the signal input from each transducer constituting the transducer array 2 and transmits the amplified signal to the AD conversion unit 18. The AD conversion unit 18 converts the signal transmitted from the amplification unit 17 into digital data and transmits the converted data to the beamformer 19. The beamformer 19 executes so-called reception focus processing in which a delay is given to each piece of data converted by the AD conversion unit 18 in compliance with a sound speed or a distribution of a sound speed based on a reception delay pattern selected according to a control signal from the apparatus controller 13 and addition is performed. With the reception focus processing, each piece of data converted by the AD conversion unit 18 is subjected to phasing addition, and a reception signal with a narrowed focus of the ultrasound echo is acquired.

Figure 3:
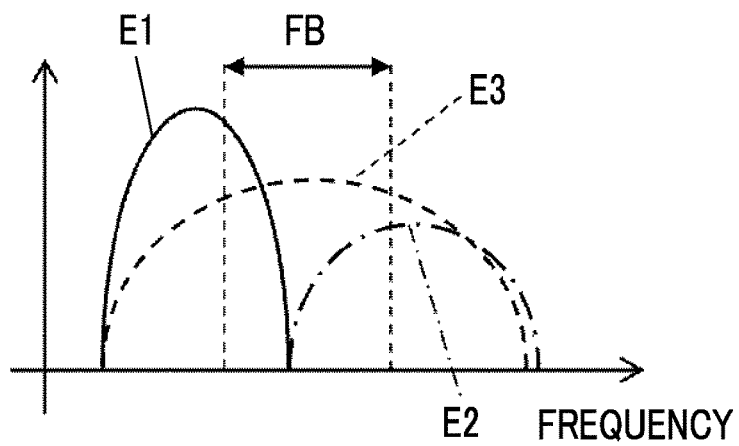
FIG. 3 is a diagram showing an example of a range of quadrature detection corresponding to a first ultrasonic pulse.
Figure 4:
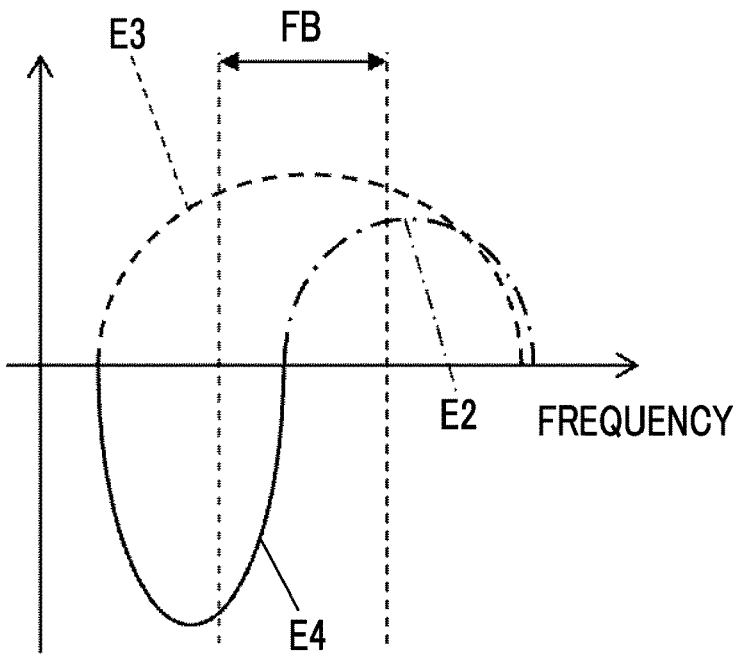
FIG. 4 is a diagram showing an example of a range of quadrature detection corresponding to a second ultrasonic pulse.

Here, the ultrasound echo propagating through the subject includes a fundamental component having a range of a fundamental wave forming the first ultrasonic pulse and the second ultrasonic pulse, a secondary harmonic component due to motion of a tissue of the subject, and a nonlinear component due to micro vibration of bubbles of the contrast medium introduced into the subject. For this reason, for example, as shown in FIGS. 3 and 4, the reception signals acquired by the reception unit 4 include a fundamental signal E1 or E4 based on the fundamental component of the ultrasound echo, a secondary harmonic signal E2 based on the secondary harmonic component, and a nonlinear signal E3 based on the nonlinear component resulting from the bubbles of the contrast medium. In the example shown in FIG. 3, a reception signal based on an ultrasonic pulse having a positive phase is shown, and the fundamental signal E1 has a positive value. On the other hand, in the example shown in FIG. 4, a reception signal based on an ultrasonic pulse having a negative phase is shown, and the fundamental signal E4 has a negative value.

The quadrature detection unit 5 of the processor 16 performs quadrature detection on the reception signals to convert the reception signals into IQ signals to be complex data by mixing a carrier signal having a reference frequency with the reception signals acquired by the reception unit 4 and acquires an IQ signal string corresponding to the first ultrasonic pulse and an IQ signal string corresponding to the second ultrasonic pulse. In this case, in order to improve the detection accuracy of the contrast medium introduced into the subject, as shown in FIGS. 3 and 4, it is desirable that the quadrature detection unit 5 compares the signal intensity of the fundamental signal E1 with the signal intensity of the secondary harmonic signal E3 and sets the range of quadrature detection so as to include a frequency at which the signal intensity of the nonlinear signal E3 due to the bubbles of the contrast medium becomes relatively large. In order to make the phase correction unit 7 correct the signals using analysis results of the fundamental signal E1 or E4 and the secondary harmonic signal E2, as shown in FIGS. 3 and 4, it is preferable that the quadrature detection unit 5 sets a range FB of quadrature detection so as to include a part of a frequency range of the fundamental signal E1 or E4 and a part of a frequency range of the secondary harmonic signal E2, in addition to a frequency at which the nonlinear signal E3 becomes the maximum.

The tissue velocity detection unit 6 of the processor 16 detects a velocity of the tissue in the subject based on the IQ signal strings acquired by the quadrature detection unit 5. In this case, the tissue velocity detection unit 6 calculates a velocity vector at each reflection position in the subject by computing autocorrelation of the IQ signal strings and detects the velocity of the tissue in the subject based on the velocity vectors. The calculation of the tissue of the subject in the tissue velocity detection unit 6 will be described below in detail.

The phase correction unit 7 of the processor 16 corrects the phase of the IQ signal string from each reflection position in the subject based on the velocity of the tissue detected by the tissue velocity detection unit 6 such that an influence of the velocity of the tissue is cancelled.

The pulse inversion addition unit 8 of the processor 16 adds the IQ signals corresponding to the first ultrasonic pulse and the IQ signals corresponding to the second ultrasonic pulse using the IQ signal strings having the phases corrected by the phase correction unit 7, thereby acquiring added signals having the fundamental signals E1 and E4 shown in FIGS. 3 and 4 eliminated.

The nonlinear signal information calculation unit 9 of the processor 16 calculates, as nonlinear signal information, at least one of power or a velocity of the nonlinear signal E3 due to the bubbles of the contrast medium introduced into the subject from the added signals acquired by the pulse inversion addition unit 8.

The image generation unit 10 of the processor 16 generates an ultrasound image based on at least one of the power or the velocity of the nonlinear signal E3 calculated by the nonlinear signal information calculation unit 9.

The display controller 11 of the processor 16 executes predetermined processing on the ultrasound image and the like and makes the display unit 12 display the ultrasound image and the like generated by the image generation unit 10 under the control of the apparatus controller 13.

The display unit 12 of the ultrasound diagnostic apparatus 1 displays an image and the like under the control of the display controller 11, and includes, for example, a display device, such as a liquid crystal display (LCD).

The operating unit 15 of the ultrasound diagnostic apparatus 1 is provided for the user performing an input operation, and can comprise a keyboard, a mouse, a trackball, a touch pad, a touch panel, and the like.

The storage unit 14 stores an operation program and the like of the ultrasound diagnostic apparatus 1, and a recording medium, such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

The processor 16 having the transmission unit 3, the reception unit 4, the quadrature detection unit 5, the tissue velocity detection unit 6, the phase correction unit 7, the pulse inversion addition unit 8, the nonlinear signal information calculation unit 9, the image generation unit 10, the display controller 11, and the apparatus controller 13 is constituted of a central processing unit (CPU) and a control program causing the CPU to execute various kinds of processing; however, the processor 16 may be constituted using a field programmable gate array (FPGA), a digital signal processor (DSP), an application specific integrated circuit (ASIC), a graphics processing unit (GPU), and other integrated circuits (ICs). The transmission unit 3, the reception unit 4, the quadrature detection unit 5, the tissue velocity detection unit 6, the phase correction unit 7, the pulse inversion addition unit 8, the nonlinear signal information calculation unit 9, the image generation unit 10, the display controller 11, and the apparatus controller 13 may be incorporated partially or entirely in one CPU or the like.

Figure 5:
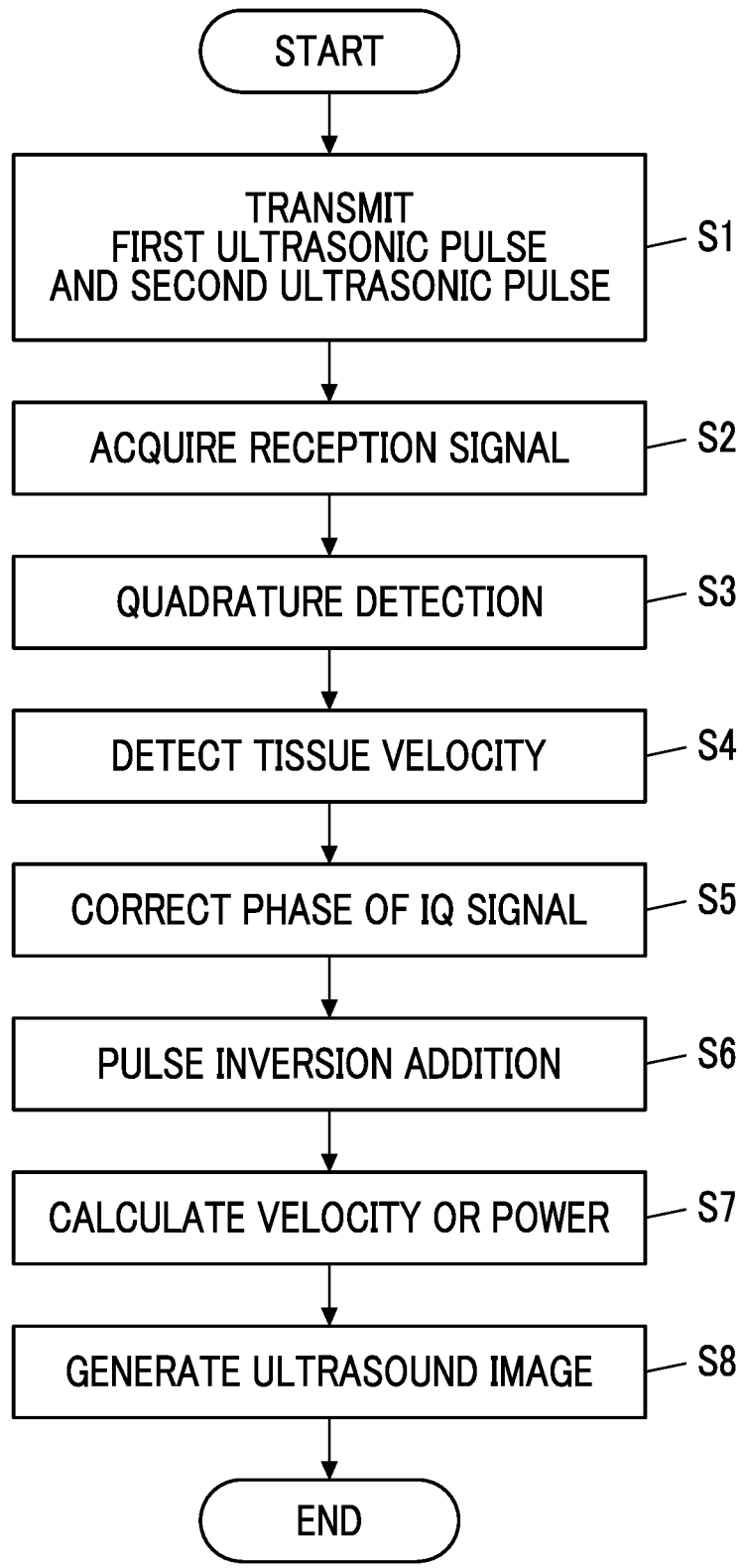
FIG. 5 is a flowchart representing the operation of the ultrasound diagnostic apparatus according to Embodiment 1 of the invention.

Next, the operation of the ultrasound diagnostic apparatus 1 in Embodiment 1 will be described in detail referring to a flowchart shown in FIG. 5. In Embodiment 1, the ultrasound diagnostic apparatus 1 sequentially transmits the first ultrasonic pulse and the second ultrasonic pulse having phases inverted from each other on the same scanning line and generates the ultrasound image using a pulse inversion method that adds a reception signal of the first ultrasonic pulse and a reception signal of the second ultrasonic pulse.

Figure 6:
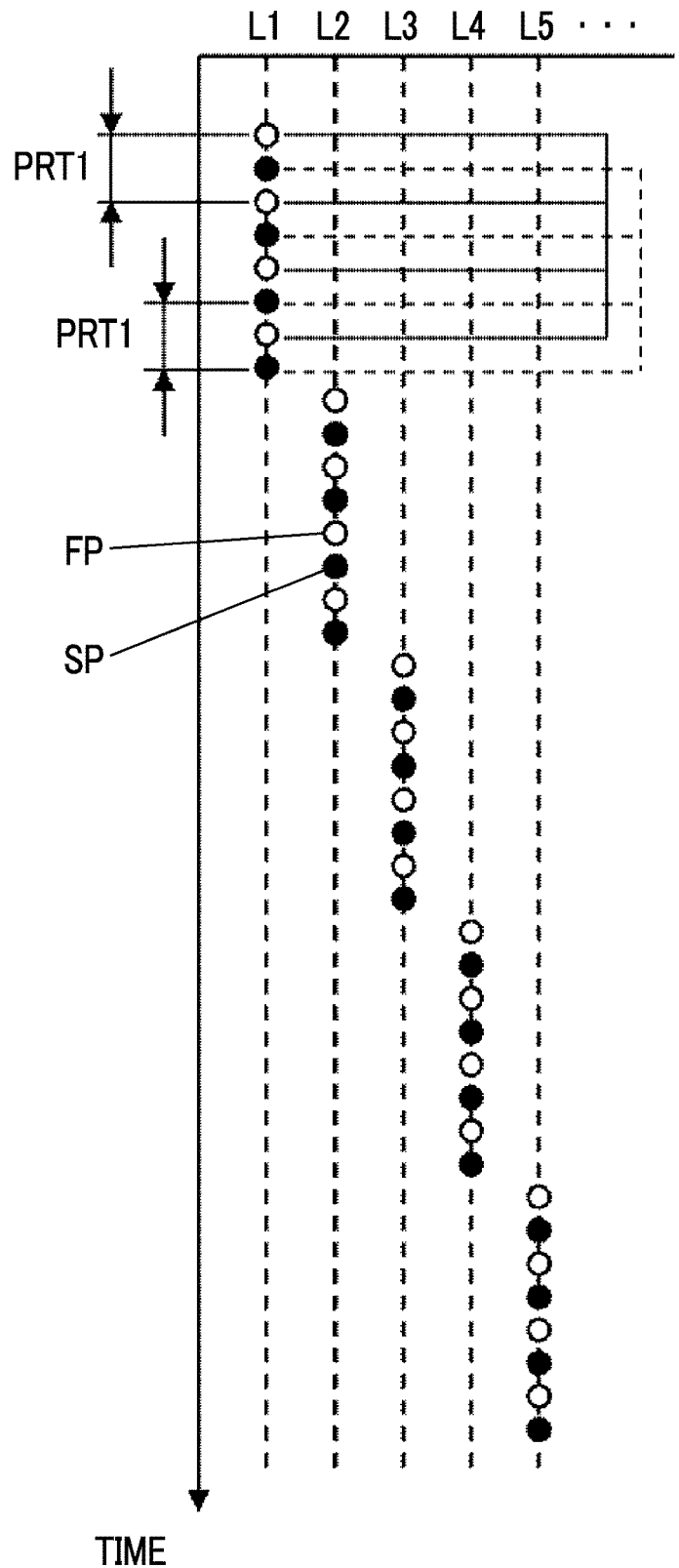
FIG. 6 is a diagram schematically showing a transmission timing of an ultrasonic pulse.

First, in Step S1, the transmission unit 3 transmits the first ultrasonic pulse and the second ultrasonic pulse having phases inverted from each other on the same scanning line multiple times through the transducer array 2. In this case, the transmission unit 3 transmits a set of the first ultrasonic pulse and the second ultrasonic pulse on the same scanning line N times, and then, transmits a set of the first ultrasonic pulse and the second ultrasonic pulse on the next scanning line N times. Here, N is an integer equal to or greater than two. For example, as shown in FIG. 6, the transmission unit 3 alternately transmits a first ultrasonic pulse FP and a second ultrasonic pulse SP on each of scanning lines L1, L2, L3, L4, and L5 four times. In the example shown in FIG. 6, a time interval PRT1 between the first ultrasonic pulses FP adjacent in time series and a time interval PRT1 between the second ultrasonic pulses SP adjacent in time series are equal to each other.

In Step S2, the reception unit 4 acquires the reception signals based on the signal output from the transducer array 2 received the ultrasound echo generated in the subject based on the first ultrasonic pulse FP and the second ultrasonic pulse SP transmitted into the subject in Step S1.

Subsequently, in Step S3, the quadrature detection unit 5 performs quadrature detection in the range FB determined for the reception signals acquired in Step S2, thereby acquiring the IQ signal string corresponding to the first ultrasonic pulse FP and the IQ signal string corresponding to the second ultrasonic pulse. In this case, for example, as shown in FIGS. 3 and 4, the quadrature detection unit 5 performs quadrature detection in the range FB including the frequency at which the nonlinear signal E3 due to the bubbles of the contrast medium becomes the maximum, a part of the frequency range of the fundamental signals E1 and E4, and a part of the frequency range of the secondary harmonic signal E2.

Figure 7:
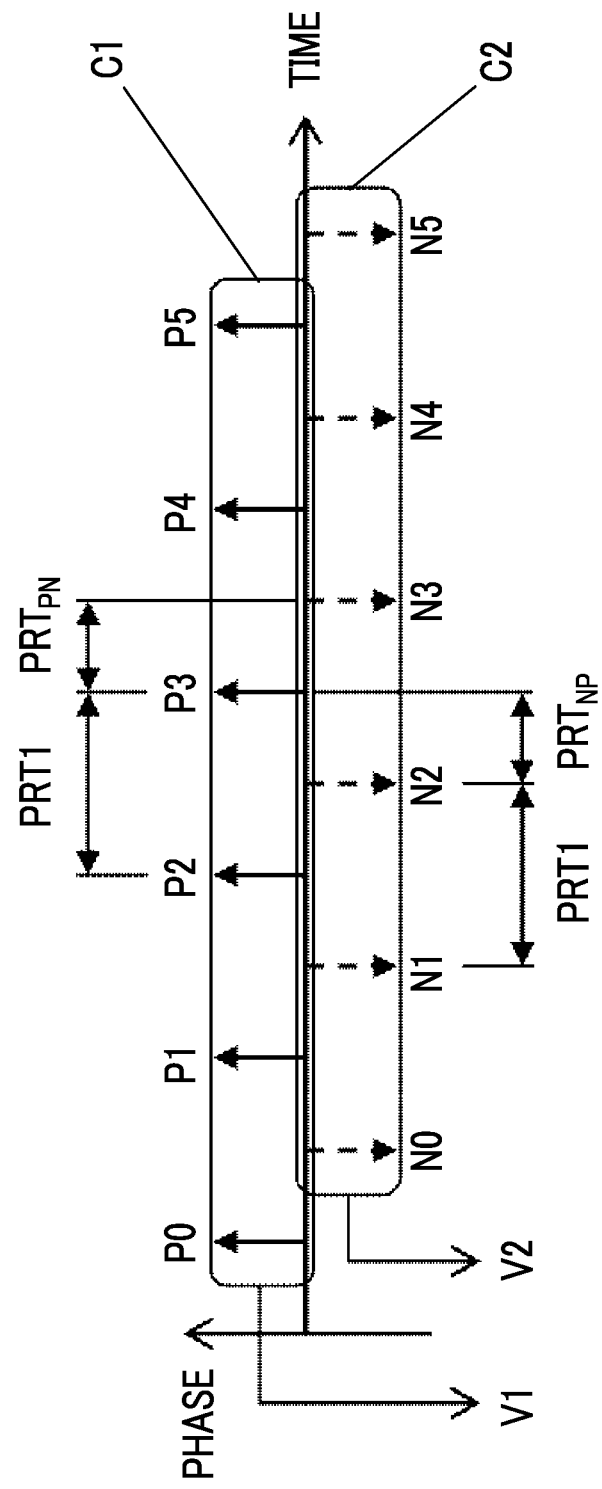
FIG. 7 is a diagram schematically showing IQ signal strings corresponding to the first ultrasonic pulse and the second ultrasonic pulse.

The IQ signal string corresponding to the first ultrasonic pulse FP and the IQ signal string corresponding to the second ultrasonic pulse SP have phases with different polarities. For example, in a case where the first ultrasonic pulse FP has a positive phase and the second ultrasonic pulse SP has a negative phase, as shown in FIG. 7, an IQ signal string C including IQ signals P0, P1, P2, P3, P4, and P5 corresponding to the first ultrasonic pulse FP has a positive phase, and an IQ signal string C2 including IQ signals N0, N1, N2, N3, N4, and N5 corresponding to the second ultrasonic pulse SP has a negative phase.

Subsequently, in Step S4, the tissue velocity detection unit 6 detects the velocity of the tissue in the subject based on the IQ signal strings acquired in Step S3. In this case, for example, as shown in FIG. 7, the tissue velocity detection unit 6 calculates a velocity vector V1 at each reflection position in the subject calculated by autocorrelation from the IQ signal string C1 having the positive phase among the IQ signals acquired in Step S3 and a velocity vector V2 at each reflection position in the subject calculated by autocorrelation from the IQ signal string C2 having the negative phase among the IQ signals acquired in Step S3.

Here, the autocorrelation of the IQ signals are computed by a product of a later IQ signal in time series and a complex conjugate of an earlier IQ signal in time series between two different IQ signals in time series. For example, the tissue velocity detection unit 6 can calculate the velocity vector V1 using Expression (1) described below and can calculate the velocity vector V2 using Expression (2) described below. Here, in Expressions (1) and (2) described below, $P^*_k$ is a complex conjugate of an IQ signal $P_k$, $N^*_k$ is a complex conjugate of an IQ signal $N_k$, and n is an integer equal to or greater than 2.

$$V1 = [\Sigma(P_{k+1} P^*_k)]/(n-1)(k=0,1,2,\ldots,n-2) \quad (1)$$

$$V2 = [\Sigma(N_{k+1} N^*_k)]/(n-1)(k=0,1,2,\ldots,n-2) \quad (2)$$

The tissue velocity detection unit 6 can detect a tissue velocity vector V representing the velocity of the tissue in the subject by computing an average value of the velocity vectors V1 and V2 as shown in Expression (3) described below.

$$V = (V1+V2)/2 \quad (3)$$

Subsequently, in Step S5, the phase correction unit 7 calculates correction phase amounts for correcting the IQ signal strings C1 and C2 obtained in Step S3 using a phase of the velocity of the tissue in the subject detected in Step S4 and corrects the IQ signal strings C1 and C2 based on the correction phase amounts.

For example, as shown in FIG. 7, a time interval between IQ signals $P_k$ and $P_{k+1}$ adjacent to each other in time series in the IQ signal string C1 and a time interval between IQ signals $N_k$ and $N_{k+1}$ adjacent to each other in the IQ signal string C2 in time series are referred to as PRT1, a time interval between the IQ signal $P_k$ and the IQ signal $N_k$ adjacent to each other in time series in the IQ signal strings C1 and C2 is referred to as $PRT_{PN}$, and a time interval between the IQ signal $N_k$ and the IQ signal $P_{k+1}$ adjacent to each other in time series is referred to as $PRT_{NP}$. In such a case, the phase correction unit 7 calculates a correction phase amount $\Phi_{NP}$ for the IQ signal string C1 using Expression (4) described below and calculates a correction phase amount $\Phi_{PN}$ for the IQ signal string C2 using Expression (5) described below. Here, $\Phi$ in Expressions (4) and (5) described below is a phase of the tissue velocity vector of the subject detected in Step S4.

$$\Phi_{NP} = (PRT_{NP}/PRT1)\Phi \quad (4)$$

$$\Phi_{PN} = (PRT_{PN}/PRT1)\Phi \quad (5)$$

The phase correction unit 7 can correct the IQ signal strings C1 and C2 by multiplying IQ signals P0 to P5 included in the IQ signal string C1 by $e^{-\Phi_{NP} i}$ and multiplying IQ signals N0 to N5 included in the IQ signal string C2 by $e^{-\Phi_{PN} i}$ using the correction phase amounts $\Phi_{NP}$ and $\Phi_{PN}$ calculated in this manner. Here, e is the base of natural logarithm, that is, a Napier's constant, and i is an imaginary unit. The IQ signal strings C1 and C2 are corrected in this way, whereby it is possible to cancel the influence of the velocity of the tissue in the subject in the IQ signal strings C1 and C2.

Subsequently, in Step S6, the pulse inversion addition unit 8 acquires added signals having the fundamental signals E1 and E4 eliminated by adding the IQ signals corresponding to the first ultrasonic pulse FP and the IQ signals corresponding to second ultrasonic pulse SP adjacent in time series using the IQ signal strings C1 and C2 with the phases corrected in Step S5.

Figure 8:
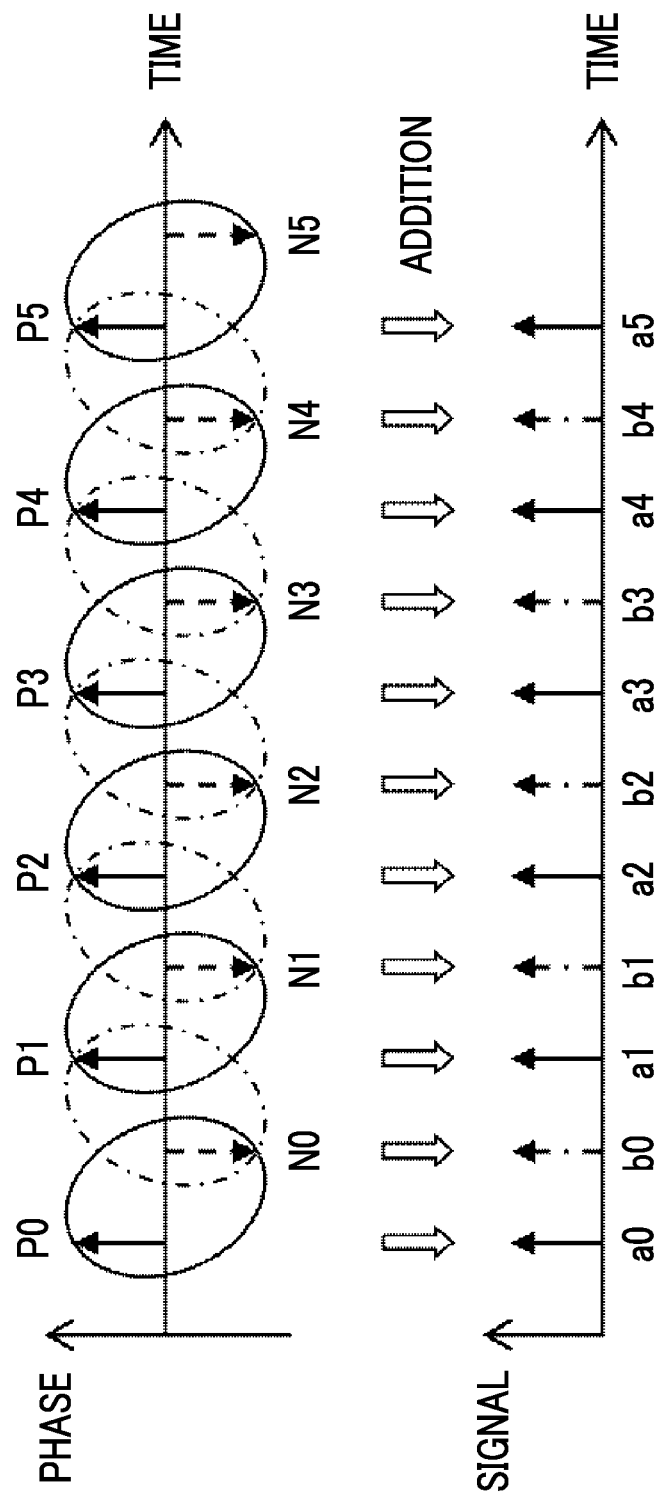
FIG. 8 is a diagram schematically showing a manner of adding the IQ signal string corresponding to the first ultrasonic pulse and the IQ signal string corresponding to the second ultrasonic pulse to calculate an added signal.

More specifically, as shown in FIG. 8, the pulse inversion addition unit 8 adds an IQ signal $P_j$ before correction in Step S5 and an IQ signal $N_j \cdot e^{-\Phi_{PN} i}$ corrected in Step S5 to calculate an added signal $a_j$ and adds an IQ signal $N_m$ before correction in Step S5 and an IQ signal $P_{m+1} \cdot e^{-\Phi_{NP} i}$ corrected in Step S5 to calculate an added signal $b_m$. In this manner, the pulse inversion addition unit 8 calculates the added signal $a_j$ as shown in Expression (6) described below and calculates the added signal $b_m$ as shown in Expression (7) described below. The added signals $a_j$ and $b_m$ calculated in this manner are signals in which the fundamental signals E1 and E4 are eliminated and the influence of the velocity of the tissue is cancelled.

$$a_j = P_j + N_j \cdot e^{-\Phi_{NP} i} (j=0,1,2,\ldots,n-1) \quad (6)$$

$$b_m = N_m + P_{m+1} \cdot e^{-\Phi_{NP} i} (m=0,1,2,\ldots,n-2) \quad (7)$$

In Step S7, the nonlinear signal information calculation unit 9 calculates at least one of power or a velocity vector of the nonlinear signal E3 due to the bubbles of the contrast medium introduced into the subject using the added signals $a_j$ and $b_m$ calculated in Step S6. For example, the nonlinear signal information calculation unit 9 calculates power PB of the nonlinear signal E3 using Expression (8) described below and calculates a velocity VB of the nonlinear signal E3 using Expression (9) described below.

$$PB = [\Sigma |a_j|^2 + \Sigma |b_m|^2]/(2n-1)(j=0,1,2,\ldots,n-1, m=0, 1, 2,\ldots,n-2) \quad (8)$$

$$VB = [\Sigma(a_{q+1} \cdot a^*_q) + \Sigma(b_{r+1} \cdot b^*_r)]/(2n-3)(q=0,1,2,\ldots,n-2, r=0, 1, 2, \ldots, n-3) \quad (9)$$

Figure 9:
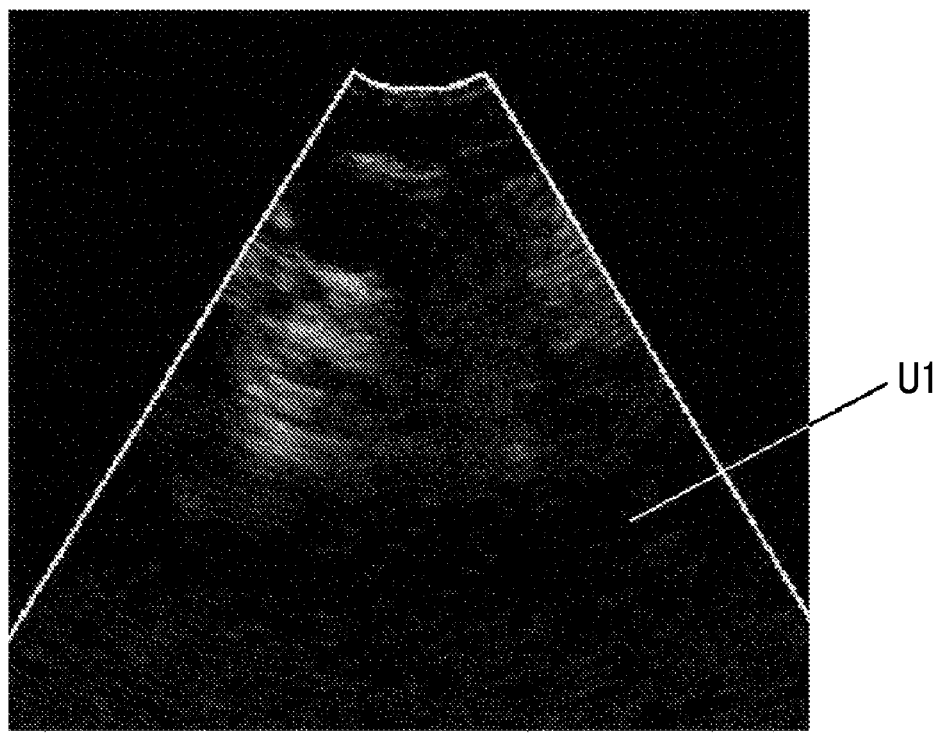
FIG. 9 is a diagram showing an example of an ultrasound image in which a value of power obtained by an ultrasound diagnostic apparatus according to Embodiment 3 of the invention is represented on a gray scale.

Subsequently, in Step S8, the image generation unit 10 generates an ultrasound image based on at least one of the power PB or the velocity VB of the nonlinear signal E3 calculated in Step S7 and displays the generated ultrasound image on the display unit 12 through the display controller 11. For example, as shown in FIG. 9, the image generation unit 10 can display an ultrasound image U1 representing the power PB of the nonlinear signal E3 calculated in Step S7 on a gray scale on the display unit 12. In this manner, the operation of the ultrasound diagnostic apparatus 1 according to Embodiment 1 of the invention ends.

Figure 10:
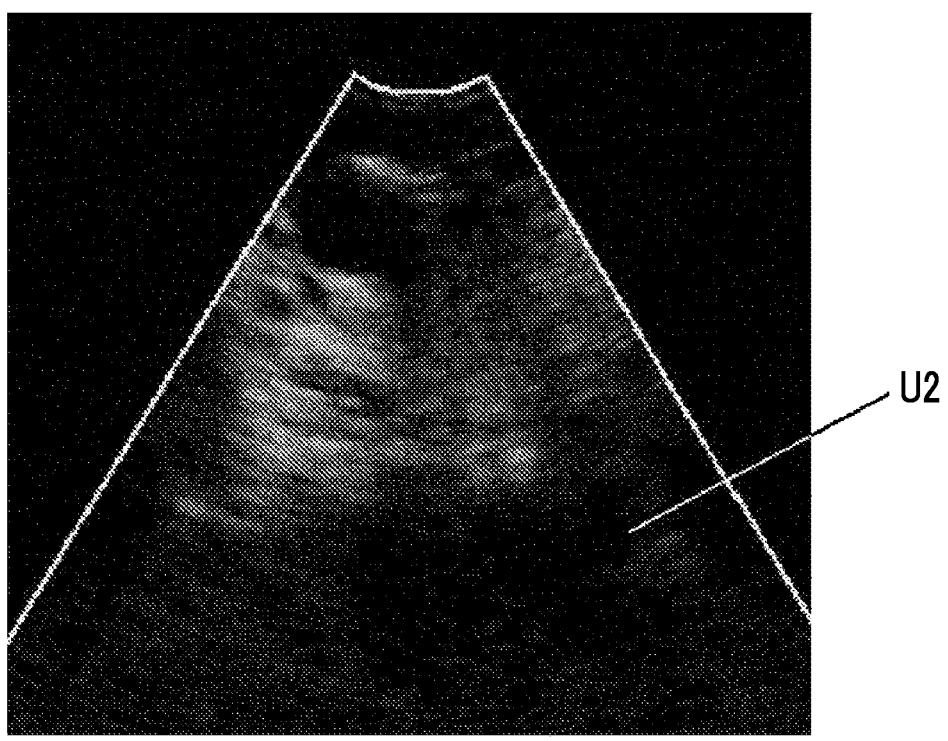
FIG. 10 is a diagram showing an example of an ultrasound image in which a value of power obtained by an ultrasound diagnostic apparatus of the related art is represented on a gray scale.

Here, as in the ultrasound diagnostic apparatus of the related art, in a case where the value of power is calculated without phase correction for the IQ signal strings C1 and C2 acquired in Step S3, an example of an ultrasound image U2 representing the calculated power on a gray scale is shown in FIG. 10. It is understood that the ultrasound image U2 shown in FIG. 10 includes more signals representing the motion of the tissue than the ultrasound image U1 shown in FIG. 9. In this way, in Embodiment 1 of the invention, since the IQ signal strings C1 and C2 are corrected in Step S5, the influence of the velocity of the tissue in the IQ signal strings C1 and C2 is cancelled, and the clear ultrasound image U1 in which the occurrence of a motion artifact is reduced is obtained.

In detecting the velocity of the tissue in the subject in Step S4, the tissue velocity detection unit 6 detects the tissue velocity vector V representing the velocity of the tissue in the subject by computing the average value of the velocity vector V1 calculated from the IQ signal string C1 having the positive phase and the velocity vector V2 calculated from the IQ signal string C2 having the negative phase; however, the detection of the velocity of the tissue is not limited thereto.

For example, the tissue velocity detection unit 6 may detect the tissue velocity vector representing the velocity of the tissue in the subject by computing autocorrelation of a given number of IQ signal strings including IQ signals having phases with different polarities among a plurality of IQ signals acquired in Step S3. However, unlike the fundamental signals E1 and E4, harmonic signals, such as the secondary harmonic signal E2 due to the motion of the tissue and the nonlinear signal E3 due to the bubbles of the contrast medium, have a positive phase without depending on the phases of the first ultrasonic pulse FP and the second ultrasonic pulse SP, whereby the influence of the harmonic signals is different between the IQ signal string C1 including the fundamental signal E1 and the IQ signal string C2 including the fundamental signal E4 having a phase with a polarity different from the fundamental signal E1. For this reason, in a case where the tissue velocity vector is calculated using the IQ signals having a phase with the same polarity, an error in the tissue velocity vector is reduced compared to a case where the tissue velocity vector using the IQ signals having phases with different polarities is calculated.

For this reason, it is preferable that the tissue velocity vector V is detected by computing autocorrelation of the IQ signal string having phases with the same polarity because an influence of reverberation noise or the like is reduced compared to a case where the tissue velocity vector is detected based on the IQ signals having phases with different polarities.

For example, the tissue velocity detection unit 6 may detect the velocity of the tissue in the subject using a velocity vector at each reflection position of the subject calculated by autocorrelation from an IQ signal string by performing subtraction of the IQ signals corresponding to the first ultrasonic pulse FP and the IQ signals corresponding to the second ultrasonic pulse SP adjacent in time series. For example, as shown in FIG. 11, the tissue velocity detection unit 6 can detect a tissue velocity vector V3 by performing subtracting IQ signals P0 to P5 having a positive phase and IQ signals N0 to N5 having a negative phase to calculate subtracted signals $d_0$ to $d_5$ and computes autocorrelation of the calculated subtracted signals $d_0$ to $d_5$.

The subtracted signals $d_0$ to $d_5$ calculated in this manner include the fundamental signals E1 and E4 while the secondary harmonic signal E2 and the nonlinear signal E3 shown in FIGS. 3 and 4 are excluded. Even in this case, in Step S5, the IQ signal strings C1 and C2 are corrected based on the tissue velocity vector V3, whereby the influence of the velocity of the tissue can be excluded from the IQ signal strings C1 and C2.

Figure 11:
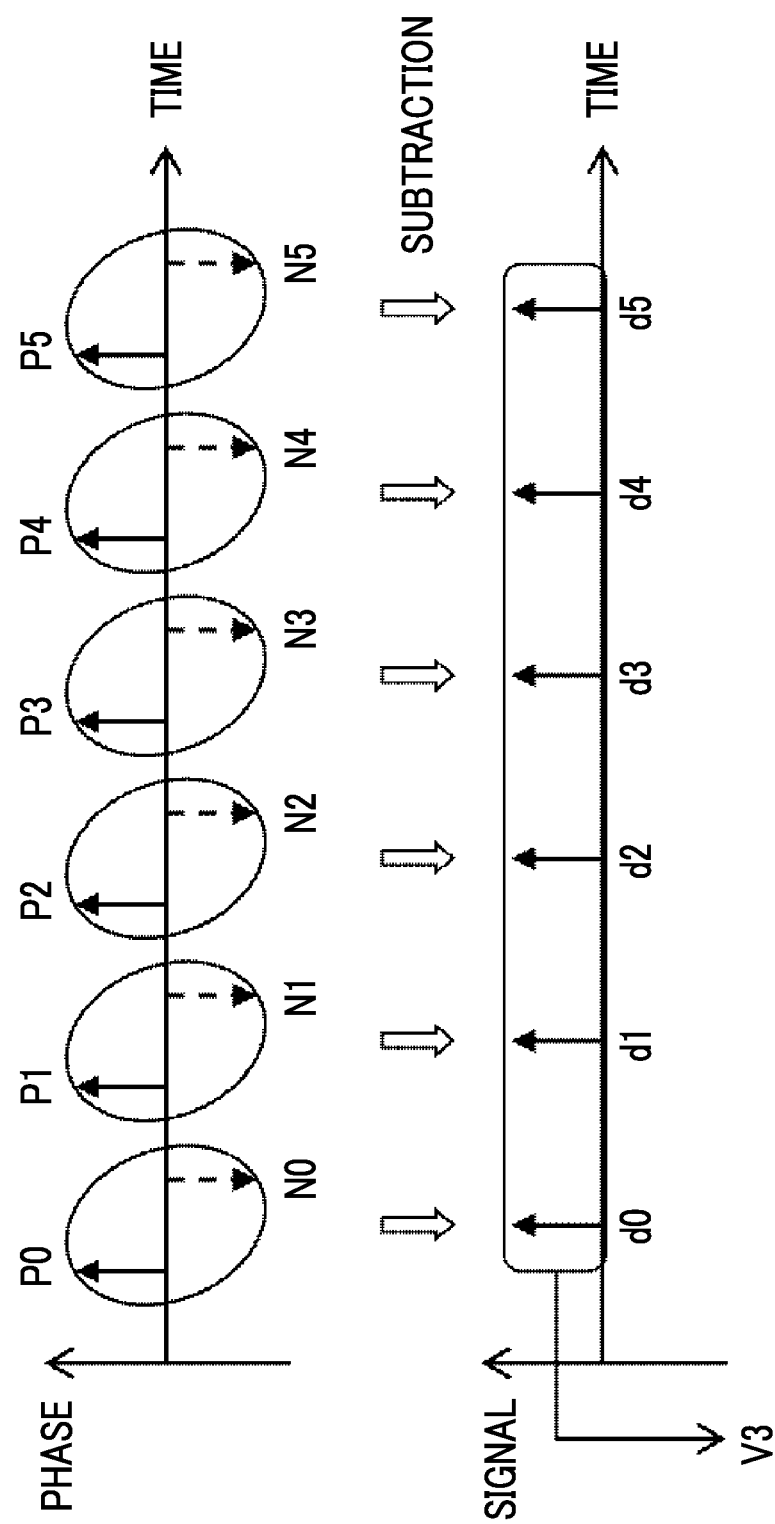
FIG. 11 is a diagram schematically showing a manner of performing subtraction of IQ signals.

In the example shown in FIG. 11, although subtraction of the IQ signal $P_k$ and the IQ signal $N_k$ is performed, subtraction of the IQ signal $N_k$ and the IQ signal $P_{k+1}$ may be performed. Alternatively, subtraction processing may be executed based on any combination of a plurality of IQ signals included in the IQ signal string and a plurality of IQ signals included in the IQ signal string C2.

In Step S5, although the phase correction unit 7 corrects the IQ signal strings C1 and C2 using the tissue velocity vector V obtained in Step S4, a correction method of the IQ signal strings C1 and C2 is not limited thereto. For example, the phase correction unit 7 can calculate correction phase amounts by calculating a phase of each of the IQ signals included in the IQ signal strings C1 and C2, calculating a difference in phase between adjacent IQ signals in the IQ signal strings C1 and C2, and computing an average value of the difference. The phase correction unit 7 can correct the IQ signal strings C1 and C2 based on the correction phase amounts calculated in this manner.

In Step S6, although the pulse inversion addition unit 8 adds the IQ signals corresponding to the first ultrasonic pulse FP and the IQ signals corresponding to the second ultrasonic pulse SP adjacent in time series, the IQ signals corresponding to the first ultrasonic pulse FP and the IQ signals corresponding to the second ultrasonic pulse SP may be added in any combination not adjacent in time series. However, it is preferable that the IQ signals corresponding to the first ultrasonic pulse FP and the IQ signals corresponding to the second ultrasonic pulse SP adjacent in time series are added because the influence of the motion of the tissue of the subject is reduced.

In Step S6, although the pulse inversion addition unit 8 calculates the added signal $a_j$ using Expression (7) and calculates the added signal $b_m$ using Expression (8), only one of the added signal $a_j$ and the added signal $b_m$ may be calculated. Even in this case, an ultrasound image in which a motion artifact is reduced can be obtained using the added signal $a_j$ or the added signal bk.

In Embodiment 1, although the ultrasound image representing the value of the power PB calculated in Step S7 on a gray scale is shown as an example of the ultrasound image generated in Step S8, an aspect of an ultrasound image is not limited thereto.

Figure 12:
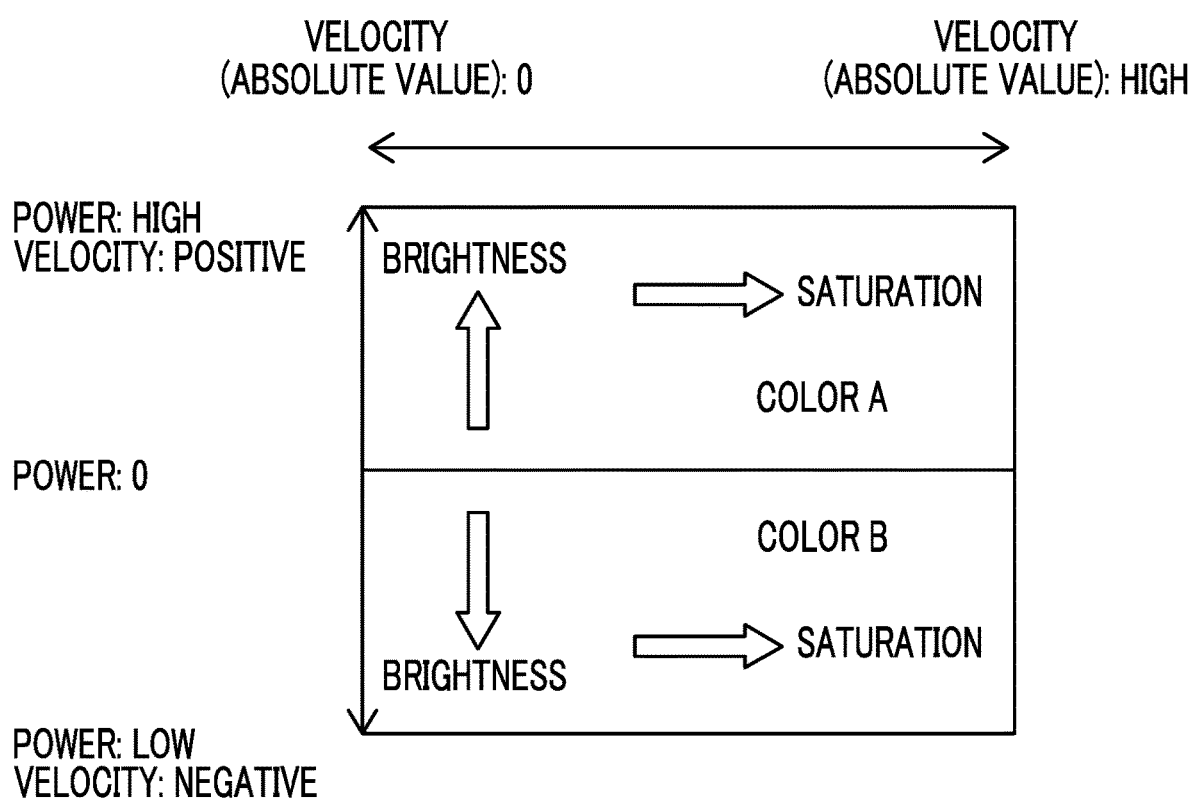
FIG. 12 is a diagram schematically showing a display example of power and a velocity obtained by the ultrasound diagnostic apparatus according to Embodiment 3 of the invention.

For example, as shown in FIG. 12, the image generation unit 10 can select one of a color A and a color B according to the polarity of the velocity VB of the nonlinear signal E3 calculated in Step S7, can represent the value of the power PB with a change in brightness, can generate an ultrasound image representing an absolute value of the velocity VB with a change in saturation, and can display the generated image on the display unit 12. In the example shown in FIG. 12, the greater the value of the power PB is, the greater the value is, in a region where the velocity VB is positive, the greater the absolute value of the velocity VB is, the higher the saturation of the color A is, and in a region where the velocity VB is negative, the greater the absolute value of the velocity VB is, the higher the saturation of the color B is. In this way, the magnitude of the value of the power PB is represented by value, and the magnitude of the absolute value of the velocity VB is represented by saturation of a given color, whereby the user can confirm the ultrasound image to ascertain the power PB and the velocity VB of the nonlinear signal E3 due to the bubbles of the contrast medium introduced into the subject.

Though not shown, a B mode processing unit that generates a B mode image is provided in the ultrasound diagnostic apparatus 1, whereby at least one of the power PB or the velocity VB of the nonlinear signal E3 due to the bubbles of the contrast medium introduced into the subject can be imaged and displayed in such a manner as to be superimposed a B mode image representing a tomographic image of the subject on the display unit 12. Alternatively, at least one of the power PB or the velocity VB of the nonlinear signal E3 due to the bubbles of the contrast medium may be imaged and displayed on the display unit 12 in parallel with the B mode image representing the tomographic image of the subject.

Embodiment 2

Figure 13:
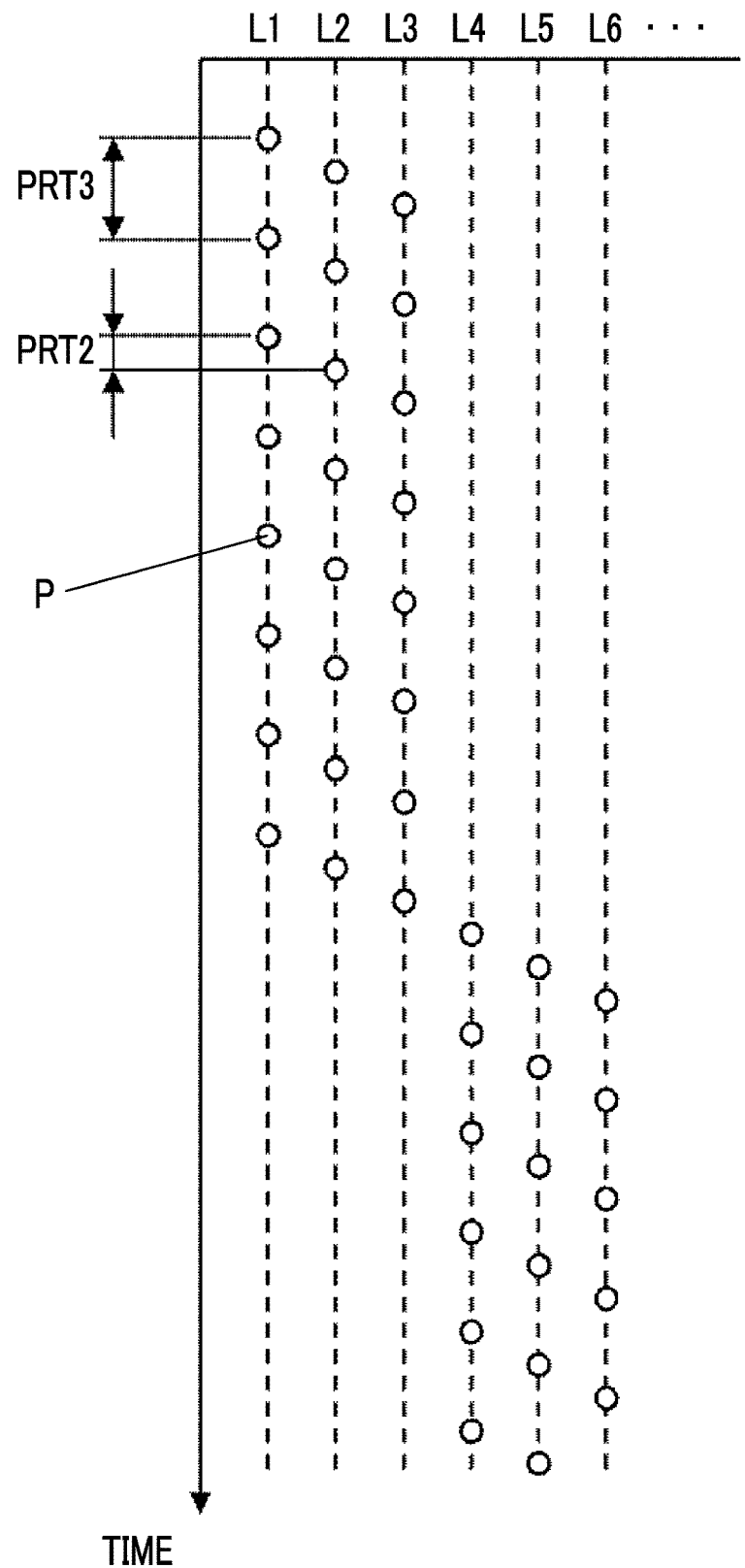
FIG. 13 is a diagram schematically showing a transmission timing of an ultrasonic pulse in interleaved scanning of the related art.

A scanning system that is carried out in an ultrasound diagnostic apparatus according to Embodiment 2 is schematically shown in FIG. 13. The scanning system is also called interleaved scanning, and since sequential transmission of ultrasonic pulses P on a determined number of scanning lines is repeated, a time interval between the ultrasonic pulses transmitted on the same scanning line can be extended while a cycle of generating an ultrasound image, that is, a frame rate can be maintained compared to a case where the ultrasonic pulses P are sequentially transmitted only on the same scanning line.

Here, in the example shown in FIG. 13, sequential transmission of the ultrasonic pulses P on three scanning lines L1, L2, and L3 is repeated eight times, and then, sequential transmission of the ultrasonic pulses P on next three scanning lines L4, L5, and L6 is repeated eight times. With this, eight ultrasonic pulses P are transmitted on each of the scanning lines L1 to L6. Although the ultrasonic pulses P are transmitted from the transducer array 2 at a time interval PRT2, a time interval between the ultrasonic pulses P adjacent in time series on the same scanning line is a time interval PRT3 greater than the time interval PRT2.

In the invention, such interleaved scanning is performed, whereby destruction of the bubbles of the contrast medium introduced into the subject can be prevented. For example, as shown in FIG. 14, the transmission unit 3 repeats one-time sequential transmission of the first ultrasonic pulse FP on a determined number of scanning lines and then one-time sequential transmission of the second ultrasonic pulse SP on the determined number of scanning lines N times, thereby transmitting a set of the first ultrasonic pulse FP and the second ultrasonic pulse SP on the determined number of scanning lines N times.

Figure 14:
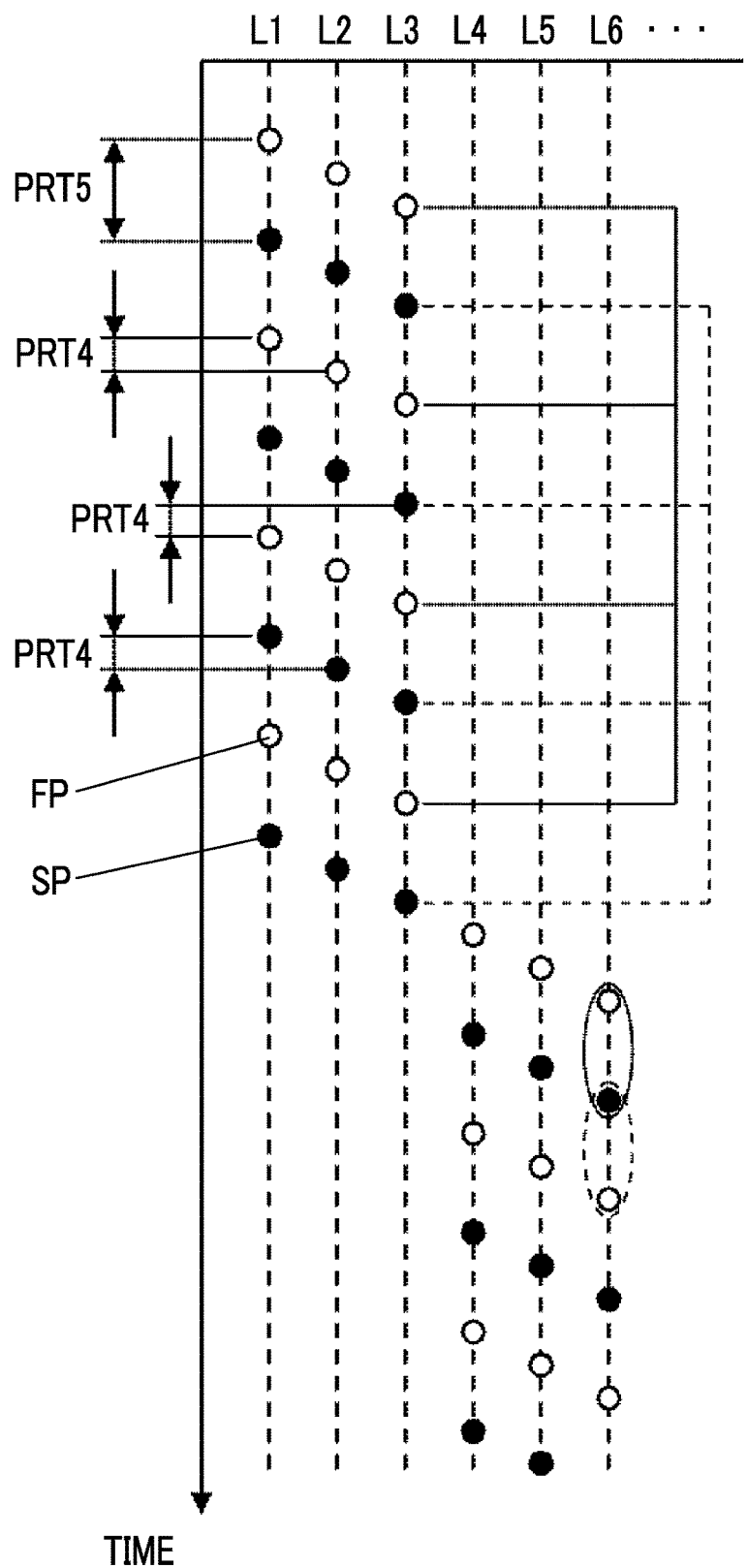
FIG. 14 is a diagram schematically showing a transmission timing of an ultrasonic pulse in Embodiment 2 of the invention.

In the example shown in FIG. 14, the transmission unit 3 repeats one-time sequential transmission of the first ultrasonic pulse FP on three scanning lines L1, L2, and L3 and then one-time sequential transmission of the second ultrasonic pulse SP on the scanning lines L1, L2, and L3 four times, and transmits the first ultrasonic pulse FP and the second ultrasonic pulse SP on the next three scanning lines L4, L5, and L6 using the same method. With this, the first ultrasonic pulse FP and the second ultrasonic pulse SP are alternately transmitted on the scanning lines L1 to L6 four times.

Although the first ultrasonic pulse FP and the second ultrasonic pulse SP are transmitted from the transducer array 2 at a time interval PRT4, a time interval between the first ultrasonic pulses FP, between the second ultrasonic pulses SP, and between the first ultrasonic pulse FP and the second ultrasonic pulse SP adjacent to each other in time series on the same scanning line is a time interval PRT5 greater than the time interval PRT4. For this reason, the transmission unit 3 performs, for example, interleaved scanning shown in FIG. 14, whereby destruction of the bubbles of the contrast medium can be prevented while the frame rate of generating the ultrasound image can be maintained.

In this way, even though the transmission unit 3 performs interleaved scanning, as in the aspect described in Embodiment 1, the IQ signal string corresponding to the first ultrasonic pulse FP and the IQ signal string corresponding to the second ultrasonic pulse SP are corrected by the phase correction unit 7, and the added signals in which the influence of the velocity of the tissue in the subject is cancelled are acquired using the corrected IQ signal strings by the pulse inversion addition unit 8. A clear ultrasound image in which the occurrence of a motion artifact is reduced is obtained based on such added signals.

Figure 15:
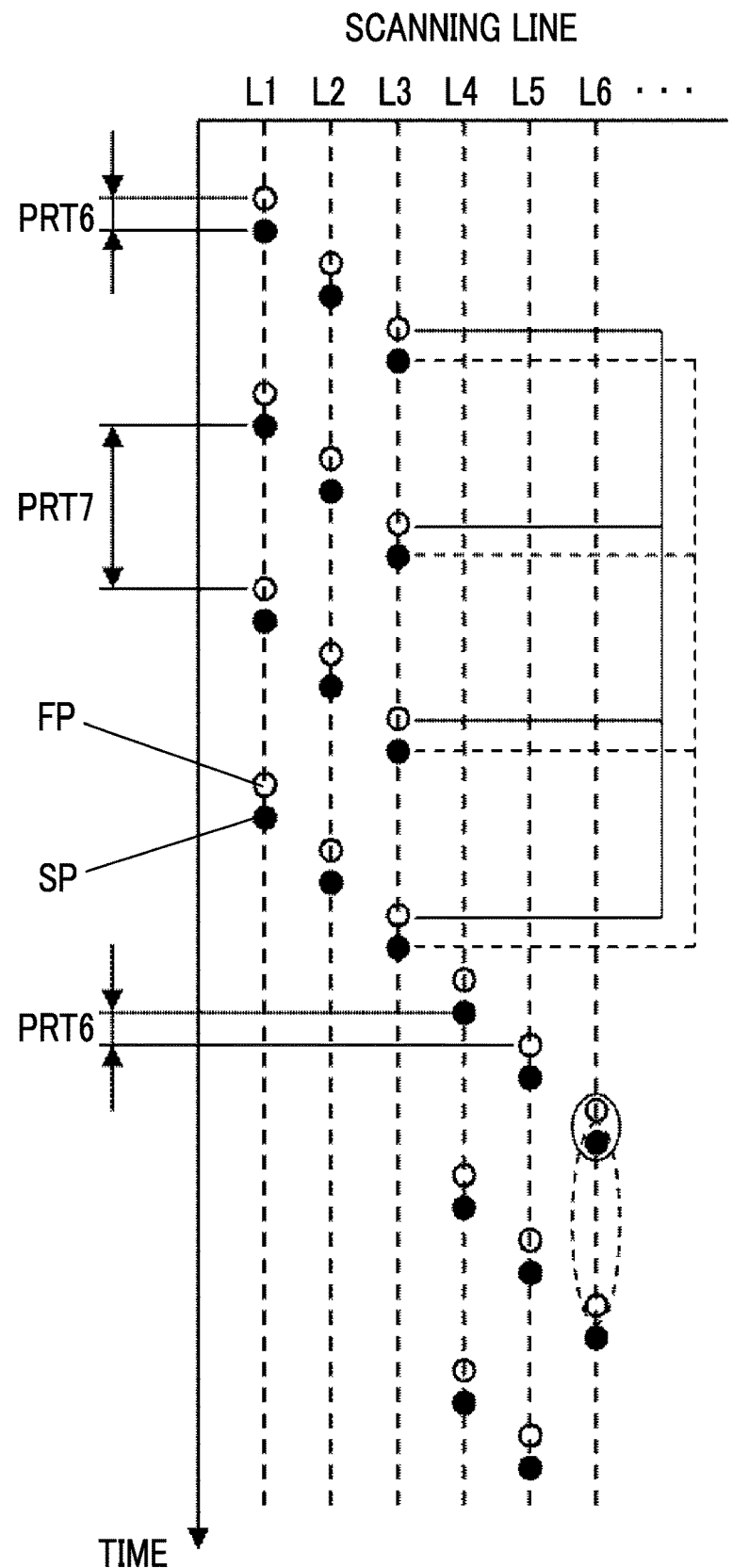
FIG. 15 is a diagram schematically showing a transmission timing of an ultrasonic pulse in a modification example of Embodiment 2 of the invention.

For example, as shown in FIG. 15, the transmission unit 3 may repeat one-time sequential transmission of a set of the first ultrasonic pulse FP and the second ultrasonic pulse SP on a determined number of scanning lines N times, thereby performing interleaved scanning for transmitting the first ultrasonic pulse FP and the second ultrasonic pulse SP on the determined number of scanning lines N times.

In the example shown in FIG. 15, the transmission unit 3 repeats one-time sequential transmission of the first ultrasonic pulse FP and the second ultrasonic pulse SP on the three scanning lines L1, L2, and L3 four times, and sequentially transmits a set of the first ultrasonic pulse FP and the second ultrasonic pulse SP on the next three scanning lines L4, L5, and L6 once. With this, the first ultrasonic pulse FP and the second ultrasonic pulse SP are alternately transmitted on the scanning lines L1 to L6 four times.

Although the first ultrasonic pulse FP and the second ultrasonic pulse SP are transmitted from the transducer array 2 at a time interval PRT6, on the same scanning line, a set of the first ultrasonic pulse FP and the second ultrasonic pulse SP is transmitted at the time interval PRT6, and then, a next set of the first ultrasonic pulse FP and the second ultrasonic pulse SP is transmitted at a time interval PRT7 greater than the time interval PRT6. For this reason, the transmission unit 3 performs, for example, interleaved scanning shown in FIG. 15, whereby destruction of the bubbles of the contrast medium can be prevented while the frame rate of generating the ultrasound image can be maintained.

Here, since the time interval PRT6 between the first ultrasonic pulse FP and the second ultrasonic pulse SP can be made to be smaller than the time interval PRT5 between the first ultrasonic pulse FP and the second ultrasonic pulse SP shown in FIG. 14, the IQ signals corresponding to the first ultrasonic pulse FP and the second ultrasonic pulse SP at the time interval PRT6 in time series are added to acquire the added signals, whereby the influence of the motion of the tissue in the subject can be reduced in the acquired added signals.

In the example shown in FIG. 15, although the transmission unit 3 sequentially transmits a set of the first ultrasonic pulse FP and the second ultrasonic pulse SP on the determined number of scanning lines once, the transmission unit 3 may perform interleaved scanning so as to sequentially transmit a combination of an arbitrary number of the first ultrasonic pulses FP and an arbitrary number of the second ultrasonic pulses SP on a determined number of scanning lines once. Even in this case, destruction of the bubbles of the contrast medium can be prevented while the frame rate of generating the ultrasound image can be maintained.

Embodiment 3

A part of the fundamental signals E1 and E4 and a part of the secondary harmonic signal E2 due to the motion of the tissue of the subject shown in, for example, FIGS. 3 and 4 remain in the added signals calculated by the pulse inversion addition unit 8 in Embodiment 1. For this reason, for example, as a filter that eliminates the fundamental signals E1 and E4 and the secondary harmonic signal E2 from the added signals is used, the influence of the motion of the tissue can be eliminated from the added signal to obtain the ultrasound image in which the occurrence of a motion artifact is more reduced.

Figure 16:
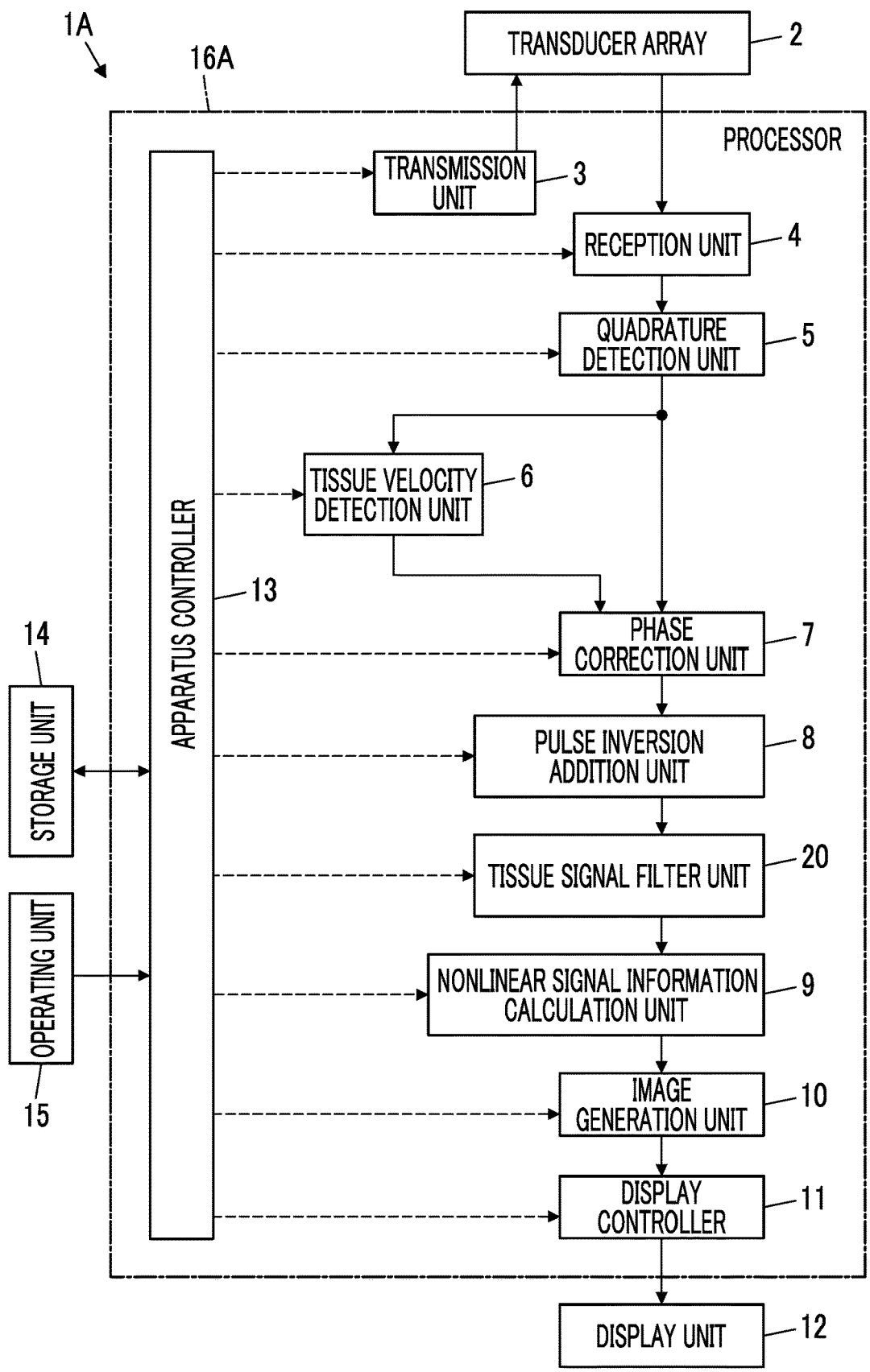
FIG. 16 is a diagram showing the configuration of the ultrasound diagnostic apparatus according to Embodiment 3 of the invention.

FIG. 16 shows the configuration of an ultrasound diagnostic apparatus 1A according to Embodiment 3. The ultrasound diagnostic apparatus 1A of Embodiment 3 has a configuration in which a tissue signal filter unit 20 is provided between the pulse inversion addition unit 8 and the nonlinear signal information calculation unit 9 in the ultrasound diagnostic apparatus 1 of Embodiment 1 shown in FIG. 1, and the tissue signal filter unit 20 is connected to the pulse inversion addition unit 8 and the nonlinear signal information calculation unit 9.

The transmission unit 3, the reception unit 4, the quadrature detection unit 5, the tissue velocity detection unit 6, the phase correction unit 7, the pulse inversion addition unit 8, the nonlinear signal information calculation unit 9, the image generation unit 10, the display controller 11, the apparatus controller 13, and the tissue signal filter unit 20 constitute a processor 16A.

The tissue signal filter unit 20 of the processor 16A is a filter that eliminates a remaining part of the fundamental signals E1 and E4 and the secondary harmonic signal E2 due to the tissue in the subject from the added signals acquired by the pulse inversion addition unit 8. For example, the tissue signal filter unit 20 performs filtering on the added signals so as to eliminate a signal near a center frequency of the secondary harmonic signal E2. Filtering of the added signals in the tissue signal filter unit 20 is different depending on a system of quadrature detection in the quadrature detection unit 5. For example, as shown in FIGS. 3 and 4, in a case where the quadrature detection unit 5 performs quadrature detection in a determined range FB, a so-called bandlimiting filter that narrows the range FB is used as the tissue signal filter unit 20. For example, in a case where the quadrature detection unit 5 performs quadrature detection for multiplying an IQ signal string of the determined range FB by a reference wave having a center frequency of the range FB to shift IQ signals in the range FB to near a zero frequency, a so-called low-pass filter that reduces a signal of a high-frequency component can be used as the tissue signal filter unit 20.

Figure 17:
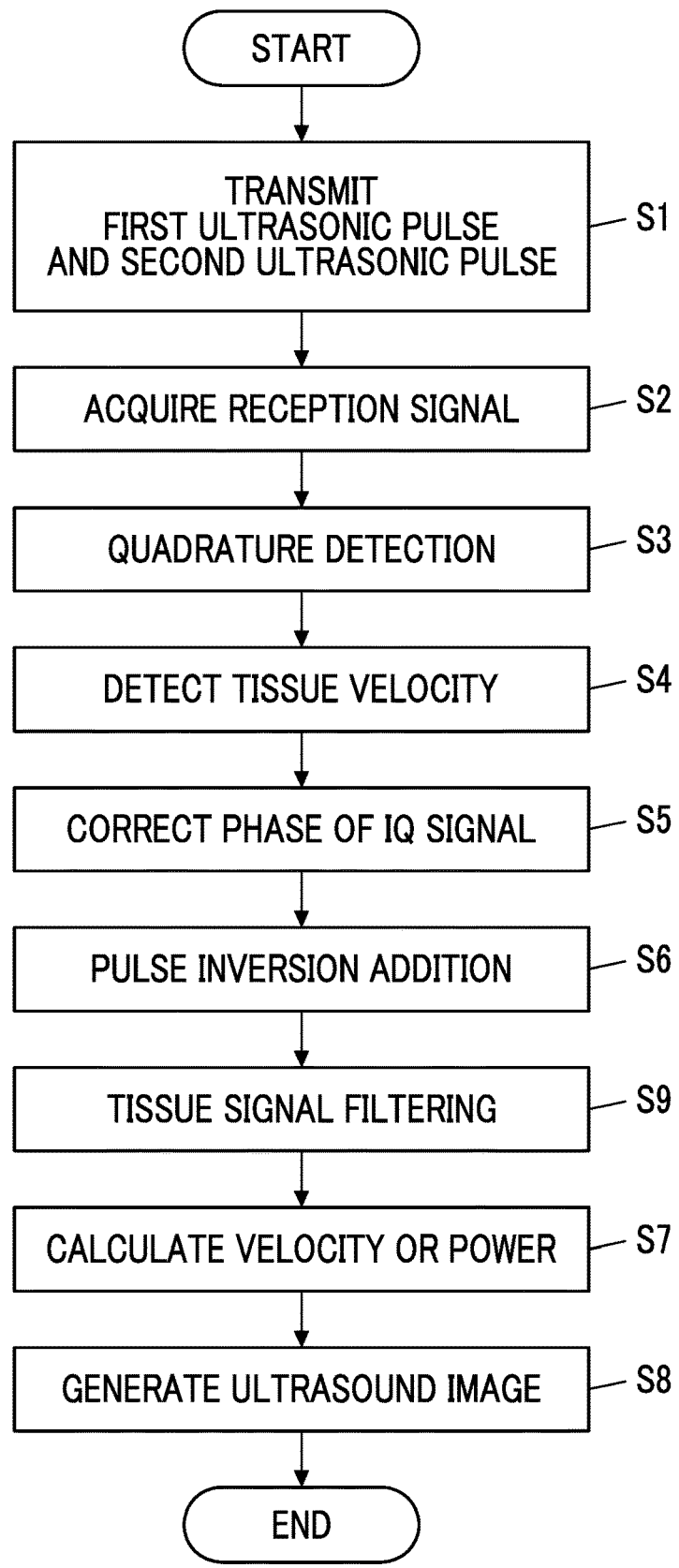
FIG. 17 is a flowchart representing the operation of the ultrasound diagnostic apparatus according to Embodiment 3 of the invention.

Next, the operation of the ultrasound diagnostic apparatus 1A according to Embodiment 3 will be described referring to a flowchart shown in FIG. 17. In the flowchart, Step S9 is added between Step S6 and Step S7 in the flowchart in Embodiment 1 shown in FIG. 5.

First, in Step S1, the transmission unit 3 transmits the first ultrasonic pulse FP and the second ultrasonic pulse SP into the subject through the transducer array 2.

Next, in Step S2, an ultrasound echo based on the first ultrasonic pulse FP and the second ultrasonic pulse SP transmitted into the subject in Step S1 is received by the transducer array 2, and reception signals are acquired based on signals output from the transducer array 2 by the reception unit 4.

In Step S3, the quadrature detection unit 5 acquires the IQ signal strings C1 and C2 corresponding to the first ultrasonic pulse FP and the second ultrasonic pulse SP by performing quadrature detection on the reception signals acquired in Step S2.

Subsequently, in Step S4, the tissue velocity detection unit 6 detects the velocity of the tissue in the subject based on the IQ signal strings acquired in Step S3. In this case, for example, the tissue velocity detection unit 6 detects the tissue velocity vector V representing the velocity of the tissue by calculating the velocity vectors V1 and V2 representing the velocity of the tissue in the subject from the IQ signal string C1 corresponding to the first ultrasonic pulse FP and the IQ signal string C2 corresponding to the second ultrasonic pulse SP, respectively, and computing the average value of the velocity vectors. In this case, the tissue velocity detection unit 6 can calculate the velocity vectors V1 and V2 representing the velocity of the tissue in the subject using Expressions (1) and (2), and can detect the tissue velocity vector V of the tissue using Expression (3).

In Step S5, the phase correction unit 7 calculates the correction phase amounts $\Phi_{NP}$ and $\Phi_{PN}$ for correcting the IQ signal strings C1 and C2 acquired in Step S3 using the phase of the tissue velocity vector V of the subject detected in Step S4, and corrects the IQ signal string C1 corresponding to the first ultrasonic pulse FP and the IQ signal string C2 corresponding to the second ultrasonic pulse SP using the calculated correction phase amounts $\Phi_N P$ and $\Phi_{PN}$. In this case, for example, the phase correction unit 7 can calculate the correction phase amounts $\Phi_{NP}$ and $\Phi_{PN}$ using Expressions (4) and (5), and can correct the IQ signal strings C1 and C2 using Expressions (6) and (7).

In Step S6, the pulse inversion addition unit 8 acquires the added signals by adding the IQ signal string corresponding to the first ultrasonic pulse FP and the IQ signal string corresponding to the second ultrasonic pulse SP using the IQ signal strings corrected in Step S5. The added signals are signals in which the fundamental signals E1 and E4 shown in FIGS. 3 and 4 due to the first ultrasonic pulse FP and the second ultrasonic pulse SP are eliminated.

Subsequently, in Step S9, the tissue signal filter unit 20 eliminates the secondary harmonic signal E2 due to the tissue in the subject from the added signals acquired in Step S6. In this case, for example, the tissue signal filter unit 20 performs filtering on the added signals so as to eliminate a signal near the center frequency of the secondary harmonic signal E2 from the added signals.

Subsequently, in Step S7, the nonlinear signal information calculation unit 9 calculates at least one of the value of the power PB or the value of the velocity VB of the nonlinear signal E3 due to the bubbles of the contrast medium introduced into the subject as nonlinear signal information using the added signals filtered in Step S9. In this case, the nonlinear signal information calculation unit 9 can use Expressions (8) and (9).

In Step S8, the image generation unit 10 generates the ultrasound image based on at least one of the value of the power PB or the value of the velocity VB of the nonlinear signal E3 calculated in Step S7 and displays the generated ultrasound image on the display unit 12. The ultrasound image generated in this manner is an image in which the influence of the secondary harmonic signal E2 is eliminated, and thus, more clearly represents the nonlinear signal E3 due to the bubbles of the contrast medium. With this, the operation of the ultrasound diagnostic apparatus 1A according to Embodiment 3 ends.

As above, with the ultrasound diagnostic apparatus 1A according to Embodiment 3, since phase correction is performed on the IQ signal strings C1 and C2 to cancel the influence of the velocity of the tissue in the subject in the IQ signal strings C1 and C2, the IQ signals with different polarities in the IQ signal strings C1 and C2 subjected to phase correction are added to acquire the added signals, and filtering for eliminating the secondary harmonic signal E2 due to the tissue in the subject is performed on the acquired added signals, the ultrasound image that more clearly represents the nonlinear signal E3 due to the bubbles of the contrast medium can be obtained.

EXPLANATION OF REFERENCES 1, 1A: ultrasound diagnostic apparatus,
2: transducer array,
3: transmission unit,
4: reception unit,
5: quadrature detection unit,
6: tissue velocity detection unit,
7: phase correction unit,
8: pulse inversion addition unit,
9: nonlinear signal information calculation unit,
10: image generation unit,
11: display controller,
12: display unit,
13: apparatus controller,
14: storage unit,
15: operating unit,
16, 16A: processor,
17: amplification unit,
18: AD conversion unit,
19: beamformer,
20: tissue signal filter unit,
A, B: color,
a0, a1, a2, a3, a4, a5, b0, b1, b2, b3, b4, b5: added signal,
C1, C2: IQ signal string,
d0, d1, d2, d3, d4, d5: subtracted signal,
E1, E4: fundamental signal,
E2: secondary harmonic signal,
E3: nonlinear signal,
FB: range,
FP: first ultrasonic pulse,
L1, L2, L3, L4, L5, L6: scanning line,
P: ultrasonic pulse,
P0, P1, P2, P3, P4, P5, N0, N1, N2, N3, N4, N5: IQ signal,
PRT1, PRT2, PRT3, PRT4, PRT5, PRT6, PRT7, PRTNP, PRTPN: time interval,
SP: second ultrasonic pulse,
U1, U2: ultrasound image,
V1, V2: velocity vector,
V3: tissue velocity vector.

What is claimed is:

1. An ultrasound diagnostic apparatus comprising:
a transducer array; and
a processor configured to
transmit a set of a first ultrasonic pulse and a second ultrasonic pulse having phases inverted from each other on the same scanning line from the transducer array into a subject N times equal to or greater than at least two times,
acquire reception signals based on a signal output from the transducer array received an ultrasound echo generated in the subject,
acquire a first IQ signal string corresponding to the first ultrasonic pulse and a second IQ signal string corresponding to the second ultrasonic pulse by performing quadrature detection on the reception signals in a determined range,
calculate a positive velocity vector at each reflection position by autocorrelation from a third IQ signal string composed by IQ signals having positive phases in the first IQ signal string and the second IQ signal string,
calculate a negative velocity vector at each reflection position by autocorrelation from a fourth IQ signal string composed by IQ signals having negative phases in the first IQ signal string and the second IQ signal string,
detect a velocity of a tissue in the subject by computing an average value of the positive velocity vector at each reflection position and the negative velocity vector at each reflection position,
correct phases of the first IQ signal string and the second IQ signal string acquired from each reflection position in the subject based on the detected velocity of the tissue such that an influence of the velocity of the tissue is cancelled,
acquire added signals with a fundamental component eliminated by adding IQ signals corresponding to the first ultrasonic pulse and IQ signals corresponding to the second ultrasonic pulse adjacent in time series using the first IQ signal string and the second IQ signal string with the corrected phases, and
generate an ultrasound image based on the added signal.

2. The ultrasound diagnostic apparatus according to claim 1,
wherein the processor is further configured to acquire the added signals by performing both of addition of the IQ signals corresponding to first ultrasonic pulse and the IQ signals corresponding to the second ultrasonic pulse immediately after IQ signals corresponding to the first ultrasonic pulse in time series and addition of the IQ signals corresponding to second ultrasonic pulse and the IQ signals corresponding to the first ultrasonic pulse immediately after the IQ signals corresponding to the second ultrasonic pulse in time series.

3. The ultrasound diagnostic apparatus according to claim 1,
wherein the processor is further configured to acquire the added signals by only one of addition of the IQ signals corresponding to first ultrasonic pulse and the IQ signals corresponding to the second ultrasonic pulse immediately after the IQ signals corresponding to the first ultrasonic pulse in time series or addition of the IQ signals corresponding to second ultrasonic pulse and the IQ signals corresponding to the first ultrasonic pulse immediately after the second ultrasonic pulse in time series.

4. The ultrasound diagnostic apparatus according to claim 1,
wherein the processor is further configured to eliminate a signal due to the tissue in the subject from the acquired added signals.

5. The ultrasound diagnostic apparatus according to claim 2,
wherein the processor is further configured to eliminate a signal due to the tissue in the subject from the acquired added signals.

6. The ultrasound diagnostic apparatus according to claim 1,
wherein the processor is further configured to calculate at least one of power or a velocity of a nonlinear signal from the acquired added signals.

7. The ultrasound diagnostic apparatus according to claim 6, wherein the processor is further amended to generate the ultrasound image based on at least one of the power or the velocity of the nonlinear signal as calculated.

8. The ultrasound diagnostic apparatus according to claim 1,
wherein the processor is further configured to transmit the set of the first ultrasonic pulse and the second ultrasonic pulse on each scanning line N times, and then, transmits the set of the first ultrasonic pulse and the second ultrasonic pulse on the next scanning line N times.

9. The ultrasound diagnostic apparatus according to claim 1,
wherein the processor is further configured to transmit the set of the first ultrasonic pulse and the second ultrasonic pulse on a determined number of scanning lines N times by repeating one-time sequential transmission of the first ultrasonic pulse on the determined number of scanning lines and then one-time sequential transmission of the second ultrasonic pulse on the determined number of scanning lines N times.

10. The ultrasound diagnostic apparatus according to claim 1,
wherein the processor is further configured to transmit the set of the first ultrasonic pulse and the second ultrasonic pulse on a determined number of scanning lines N times by repeating one-time sequential transmission of the set of the first ultrasonic pulse and the second ultrasonic pulse on the determined number of scanning lines N times.

11. The ultrasound diagnostic apparatus according to claim 1, further comprising:
a display unit configured to display the ultrasound image.

12. A method of controlling an ultrasound diagnostic apparatus, the method comprising:
transmitting a set of a first ultrasonic pulse and a second ultrasonic pulse having phases inverted from each other on the same scanning line from a transducer array into a subject N times equal to or greater than at least two times;
acquiring reception signals based on a signal output from the transducer array received an ultrasound echo generated in the subject;
acquiring a first IQ signal string corresponding to the first ultrasonic pulse and a second IQ signal string corresponding to the second ultrasonic pulse by performing quadrature detection in a determined range on the acquired reception signals;
calculating a positive velocity vector at each reflection position by autocorrelation from a third IQ signal string composed by IQ signals having positive phases in the first IQ signal string and the second IQ signal string;
calculating a negative velocity vector at each reflection position by autocorrelation from a fourth IQ signal string composed by IQ signals having negative phases in the first IQ signal string and the second IQ signal string;
detecting a velocity of a tissue in the subject by computing an average value of the positive velocity vector at each reflection position and the negative velocity vector at each reflection position;
correcting phases of the first IQ signal string and the second IQ signal string acquired from each reflection position in the subject based on the detected velocity of the tissue such that an influence of the velocity of the tissue is cancelled;
acquiring added signals with a fundamental component eliminated by adding IQ signals corresponding to the first ultrasonic pulse and IQ signals corresponding to the second ultrasonic pulse adjacent in time series using the first IQ signal string and the second IQ signal string with the phases corrected; and
generating an ultrasound image based on the added signals.

\* \* \* \* \*